(12) United States Patent
Wierzbicki et al.

(10) Patent No.: US 6,627,650 B2
(45) Date of Patent: Sep. 30, 2003

(54) INDENOINDOLONE COMPOUNDS

(75) Inventors: Michel Wierzbicki, L'Etang la Ville (FR); Marie-Françoise Boussard, Mareil sur Mauldre (FR); Anne Rousseau, Longjumeau (FR); Ghanem Atassi, Saint Cloud (FR); John Hickman, Paris (FR); Alain Pierre, Les Alluets le Roi (FR); Stéphane Leonce, Versailles (FR); Nicolas Guilbaut, La Celle Saint Cloud (FR); Laurence Kraus-Berthier, Colombes (FR)

(73) Assignee: Les Laboratoires Servier, Neuilly-sur-Seine (FR)

( * ) Notice: Subject to any disclaimer, the term of this patent is extended or adjusted under 35 U.S.C. 154(b) by 0 days.

(21) Appl. No.: 10/171,191

(22) Filed: Jun. 13, 2002

(65) Prior Publication Data

US 2003/0125369 A1 Jul. 3, 2003

(30) Foreign Application Priority Data

Jun. 13, 2001 (FR) .............................. 01 07718

(51) Int. Cl.[7] ....................... A61K 31/40; C07D 209/58
(52) U.S. Cl. ....................... 514/410; 548/420
(58) Field of Search ................. 548/127, 491, 548/420; 546/201, 232, 251; 568/584; 514/323, 339, 361, 410

(56) References Cited

U.S. PATENT DOCUMENTS 6,465,660 B1 * 10/2002 Wierzbicki et al. ......... 548/420

* cited by examiner

Primary Examiner—Cecilia Tsang
Assistant Examiner—Ebenezer Sackey
(74) Attorney, Agent, or Firm—The Firm of Hueschen and Sage

(57) ABSTRACT

A compound of formula (I):

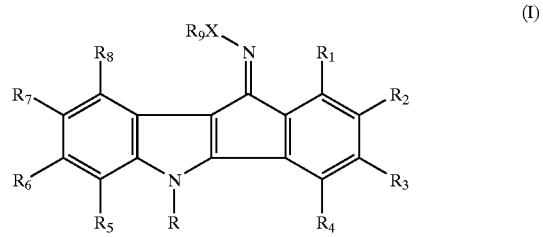

wherein:

R represents hydrogen, optionally substituted alkyl or alkenyl, $R_1$ to $R_8$, which may be identical or different, each represents hydrogen, optionally substituted alkyl, hydroxy, acyloxy, optionally substituted amino, carboxy, optionally substituted alkoxy, or alkenyloxy, or one of $R_1$ to $R_8$ forms, with another of $R_1$ to $R_8$ that is adjacent, an alkylenedioxy group, X represents oxygen or $NR_{16}$ wherein $R_{16}$ represents hydrogen, alkyl, aryl or arylalkyl, $R_9$ represents hydrogen, aryl, heteroaryl, or optionally substituted, saturated or unsaturated alkyl, an isomer thereof, or an addition salt thereof with a pharmaceutically acceptable acid or base.

Medicinal products containing the same which are useful as anti-cancer agents.

12 Claims, No Drawings

INDENOINDOLONE COMPOUNDS

DESCRIPTION OF THE PRIOR ART

The compounds of the present invention are new.

BACKGROUND OF THE INVENTION

Anti-cancer therapeutic requirements call for the constant development of new anti-tumour agents with the aim of obtaining medicaments that are simultaneously more active and better tolerated.

In addition to the fact that the compounds of the invention are new, they exhibit anti-tumour properties that are of special interest.

DETAILED DESCRIPTION OF THE INVENTION

The present invention relates more specifically to the compounds of formula (I):

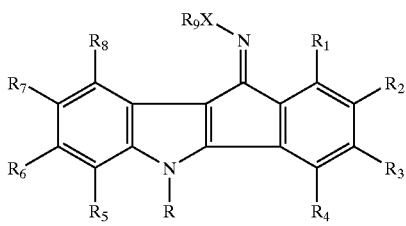

wherein:
R represents:
  a hydrogen atom,
  a linear or branched ($C_1$–$C_6$)alkyl group optionally substituted by a carboxy group, by a linear or branched ($C_1$–$C_6$)alkoxycarbonyl group or by a $NR_{10}R_{11}$ group (wherein $R_{10}$ and $R_{11}$, which may be identical or different, each represents a linear or branched ($C_1$–$C_6$)alkyl group or together, with the nitrogen carrying them, form a nitrogen-containing heterocycle),
  or a linear or branched ($C_1$–$C_6$)alkenyl group,
$R_1$ to $R_8$, which may be identical or different, each represents:
  a hydrogen atom,
  a linear or branched ($C_1$–$C_6$)alkyl group optionally substituted by an aryl, carboxy or linear or branched ($C_1$–$C_6$)alkoxycarbonyl group,
  a hydroxy group,
  a linear or branched ($C_1$–$C_6$)acyloxy group,
  a group of formula $NR_{12}R_{13}$, wherein $R_{12}$ and $R_{13}$, which may be identical or different, each represents a hydrogen atom or a linear or branched ($C_1$–$C_6$) alkyl group optionally substituted by a group of formula $NR_{14}R_{15}$, wherein $R_{14}$ and $R_{15}$, which may be identical or different, each represents a linear or branched ($C_1$–$C_6$)-alkyl group or together, with the nitrogen atom carrying them, form a nitrogen-containing heterocycle,
  a carboxy group,
  a linear or branched ($C_1$–$C_6$)alkoxy group optionally substituted by an aryl group or by a group of formula $NR_{14}R_{15}$, wherein $R_{14}$ and $R_{15}$, which may be identical or different, each represents a linear or branched ($C_1$–$C_6$)alkyl group or together, with the nitrogen atom carrying them, form a nitrogen-containing heterocycle,
  a linear or branched ($C_1$–$C_6$)alkenyloxy group,
  or one of the groups $R_1$ to $R_8$ forms, with another of the groups $R_1$ to $R_8$ that is adjacent, a ($C_1$–$C_2$) alkylenedioxy group,
X represents an oxygen atom or an $NR_{16}$ group, wherein $R_{16}$ represents a hydrogen atom or a linear or branched ($C_1$–$C_6$)alkyl group, an aryl group or an aryl-($C_1$–$C_6$) alkyl group in which the alkyl moiety may be linear or branched,
$R_9$ represents a hydrogen atom or an aryl, heteroaryl, or linear or branched ($C_1$–$C_6$)alkyl group, wherein the alkyl group optionally contains one or more unsaturations and is optionally substituted by one or more identical or different groups selected from aryl, heteroaryl, ($C_3$–$C_8$)cycloalkyl, cyano and $NR_{17}R_{18}$ (wherein $R_{17}$ and $R_{18}$, which may be identical or different, each represents a linear or branched ($C_1$–$C_6$) alkyl group or together, with the nitrogen atom carrying them, form a nitrogen-containing heterocycle),
to isomers thereof, and also to addition salts thereof with a pharmaceutically acceptable acid or base.

Isomers are to be understood as optical isomers and geometrical isomers of the C=N X $R_9$ double bond.

Among the pharmaceutically acceptable acids there may be mentioned, without implying any limitation, hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid, camphoric acid, etc.

Among the pharmaceutically acceptable bases there may be mentioned, without implying any limitation, sodium hydroxide, potassium hydroxide, triethylamine, tert-butylamine, etc.

An aryl group is to be understood as phenyl, biphenylyl or naphthyl, each of those groups optionally being substituted by one or more identical or different groups selected from halogen, linear or branched ($C_1$–$C_6$)alkyl (optionally substituted by one or more halogen atoms), linear or branched ($C_1$–$C_6$)alkenyl (optionally substituted by a phenyl group), linear or branched ($C_1$–$C_6$)alkoxy (optionally substituted by a phenyl group), phenoxy, nitro, cyano, amino (optionally substituted by one or two linear or branched ($C_1$–$C_6$)alkyl groups) and ($C_1$–$C_2$)alkylenedioxy.

A heteroaryl group is to be understood as an aromatic mono- or bi-cyclic group having from 5 to 12 ring members containing one, two or three hetero atoms selected from oxygen, nitrogen and sulphur, wherein the heteroaryl may optionally be substituted by one or more identical or different groups selected from halogen, linear or branched ($C_1$–$C_6$)-alkyl, hydroxy, linear or branched ($C_1$–$C_6$)alkoxy, linear or branched ($C_1$–$C_6$)polyhaloalkyl, and amino (optionally substituted by one or more linear or branched ($C_1$–$C_6$)alkyl groups). Amongst the heteroaryl groups the following groups may be mentioned without implying any limitation: thienyl, pyridyl, furyl, pyrrolyl, imidazolyl, oxazolyl, isoxazolyl, thiazolyl, isothiazolyl, quinolyl, isoquinolyl, pyrimidinyl, thiadiazolyl.

Preferred heteroaryl groups are thienyl, pyridyl, furyl and thiadiazolyl groups.

A nitrogen-containing heterocycle is to be understood as a saturated monocyclic group having from 5 to 7 ring members containing one, two or three hetero atoms, one of those hetero atoms being a nitrogen atom, and the additional hetero atom or atoms optionally present being selected from the atoms oxygen, nitrogen and sulphur. Preferred nitrogen-containing heterocycles are the groups pyrrolidinyl, piperidyl, morpholinyl and piperazinyl.

Preferred compounds of formula (I) are those wherein X represents an oxygen atom.

Preferred compounds of formula (I) are those wherein $R_1$ to R6 and $R_8$, which may be identical or different, each represents a hydrogen atom, a hydroxy group or a linear or branched $(C_1-C_6)$alkoxy group.

Preferred compounds of formula (I) are those wherein $R_7$ represents a 2-dimethylaminoethoxy group or a 2-(1-pyrrolidinyl)-ethoxy group.

Amongst the preferred compounds of formula (I), the following, more especially, may be mentioned:

(10Z)-8-(2-dimethylaminoethoxy)-2,3-dimethoxyindeno[1,2-b]indole-10(5H)-one O-(1-phenyl-2-propynyl)oxime, isomers thereof, and addition salts thereof with a pharmaceutically acceptable acid, (10Z)-8-(2-dimethylaminoethoxy)-2,3-dimethoxyindeno[1,2-b]indole-10(5H)-one O-(2-propynyl)oxime, isomers thereof, and addition salts thereof with a pharmaceutically acceptable acid, (10Z)-8-(2-dimethylaminoethoxy)-2,3-dimethoxyindeno[1,2-b]indole-10(5H)-one O-(1-methyl-2-propynyl)oxime, isomers thereof, and addition salts thereof with a pharmaceutically acceptable acid, (10Z)-8-(2-dimethylaminoethoxy)-2,3-dimethoxyindeno[1,2-b]indole-10(5H)-one O-[1-(3-furyl)-2-propynyl]oxime, isomers thereof, and addition salts thereof with a pharmaceutically acceptable acid, (10Z)-8-(2-(1-pyrrolidinyl)ethoxy)-2,3-dimethoxyindeno[1,2-b]indole-10(5H)-one O-[1-(3-furyl)-2-propynyl]oxime, isomers thereof, and addition salts thereof with a pharmaceutically acceptable acid, and (10Z)-8-(2-dimethylaminoethoxy)-2,3-dimethoxyindeno[1,2-b]indole-10(5H)-one O-((1S)-1-methyl-2-propynyl)oxime, isomers thereof, and addition salts thereof with a pharmaceutically acceptable acid.

The invention extends also to a process for the preparation of compounds of formula (I) which is characterised in that a compound of formula (II):

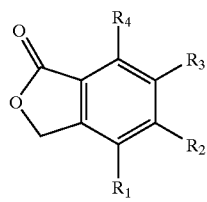

(II)

wherein $R_1$, $R_2$, $R_3$ and $R_4$ are as defined for formula (I), is reacted with N-bromosuccinimide to yield a compound of formula (III):

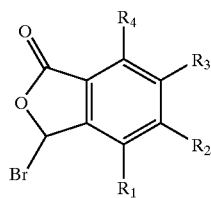

(III)

wherein $R_1$, $R_2$, $R_3$ and $R_4$ are as defined hereinbefore, which is reacted with triphenylphosphine to yield a compound of formula (IV):

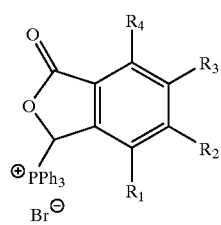

(IV)

wherein $R_1$, $R_2$, $R_3$ and $R_4$ are as defined hereinbefore, which is reacted with a compound of formula (V):

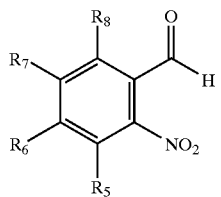

(V)

wherein $R_1$, $R_6$, $R_7$ and $R_8$ are as defined for formula (I), to yield a compound of formula (VI):

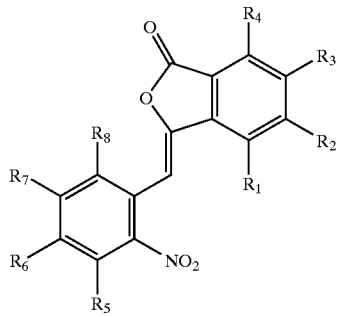

(VI)

wherein $R_1$, $R_2$, $R_3$, $R_4$, $R_5$, $R_6$, $R_7$ and $R_8$ are as defined hereinbefore, which is placed in the presence of a base to yield a compound of formula (VII):

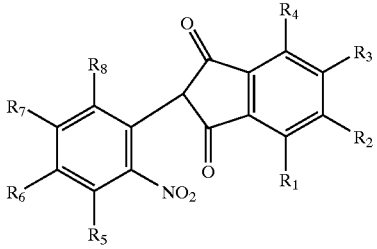

(VII)

wherein $R_1$, $R_2$, $R_3$, $R_4$, $R_5$, $R_6$, $R_7$ and $R_8$ are as defined hereinbefore,
which is subjected to the action of a reducing agent to yield, after separation of isomers where necessary, a compound of formula (VIII):

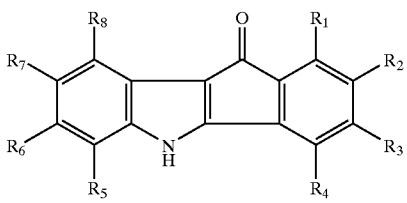

(VIII)

wherein $R_1$, $R_2$, $R_3$, $R_4$, $R_5$, $R_6$, $R_7$ and $R_8$ are as defined hereinbefore,
which is reacted, if desired, with a compound of formula (IX):

$$R'—Z \quad (IX)$$

wherein R' represents a linear or branched ($C_1$–$C_6$)alkyl group (optionally substituted by an aryl group or by an $NR_9R_{10}$ group, wherein $R_9$ and $R_{10}$, which may be identical or different, each represents a linear or branched ($C_1$–$C_6$)alkyl group or together, with the nitrogen atom carrying them, form a nitrogen-containing heterocycle) or a linear or branched ($C_1$–$C_6$) alkenyl group, and Z represents a leaving group, such as, for example, a halogen atom or a mesylate, tosylate or trifluoromethanesulphonate group,
to yield a compound of formula (X):

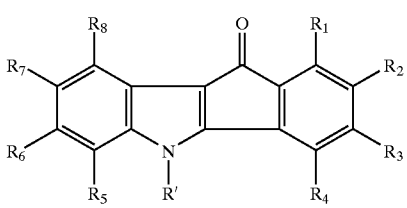

(X)

wherein $R_1$, $R_2$, $R_3$, $R_4$, $R_5$, $R_6$, $R_7$, $R_8$ and R' are as defined hereinbefore,
which compounds of formula (VIII) or (X) are reacted with a compound of formula (XI):

$$H_2NXR_9 \quad (XI)$$

wherein X and $R_9$ are as defined for formula (I),
to yield a compound of formula (I) which is purified, if necessary, according to a conventional purification technique, is separated, if desired, into isomers according to a conventional separation technique and is converted, if desired, into addition salts with a pharmaceutically acceptable acid or base.

The compound of formula (XI) can be obtained, either starting from the compound of formula (XII):

$$R_9—XH \quad (XII),$$

wherein X and $R_9$ are as defined hereinbefore,
in accordance with the procedure described in Synthesis 1976, pp. 682–683 or in Synthesis 1980, pp.461,
or starting from the compound of formula (XIII)

$$R_9—Cl \quad (XIII)$$

wherein $R_9$ is as defined hereinbefore,
in accordance with the procedure described in Tet. Lett. 1997, 38, p. 7233.

In addition to the fact that the compounds of the present invention are new, they exhibit valuable pharmacological properties. They have cytotoxic properties, which render then useful in the treatment of cancers The invention extends also to pharmaceutical compositions comprising as active ingredient at least one compound of formula (I) together with one or more appropriate, inert, non-toxic excipients. Amongst the pharmaceutical compositions according to the invention there may be mentioned more especially those which are suitable for oral, parenteral (intravenous, intramuscular or subcutaneous) or nasal administration, tablets or dragees, sublingual tablets, gelatin capsules, lozenges, suppositories, creams, ointments, dermal gels, injectable preparations, drinkable suspensions etc.

The useful dosage is adaptable in accordance with the nature and severity of the disorder, the administration route, the age and weight of the patient, and any associated treatments.

It varies from 0.5 mg to 2 g per 24 hours taken in one or more administrations.

The Examples which follow illustrate the invention but do not limit it in any way.

The starting materials employed are known products or products prepared in accordance with known procedures.

Preparations A to E result in synthesis intermediates for use in the preparation of the compounds of the invention.

The structures of the compounds described in the Examples were determined according to customary spectrometric techniques (infra-red, NMR, mass spectrometry).

Preparation A: 5-(2-Dimethylaminoethoxy)-2-nitrobenzaidehyde 10 mmol of 5-hydroxy-2-nitrobenzaldehyde dissolved in dimethylformamide are added dropwise to 20 mmol of potassium carbonate suspended in a mixture of dimethylformamide and isopropyl ether, and then the reaction mixture is heated at reflux for 2 hours. After the mixture has returned to ambient temperature, 10 mmol of 2-chloro-N,N-dimethylethanamine hydrochloride are added dropwise, and then the reaction mixture is heated at reflux again for one night. After returning to ambient temperature, the mixture is filtered and the solvents of the filtrate are evaporated off to yield the expected product in the form of an oil.

Preparation B: 2-Nitro-5-[2-(piperid-1-yl)ethoxy]benzaldehyde

The expected product is obtained in accordance with the procedure described in Preparation A, starting from 5-hydroxy-2-nitrobenzaldehyde and 1-(2-chloroethyl)-piperidine hydrochloride.

Preparation C: 2-Nitro-5-(pyrrolidin-1-ylethoxy) benzaldehyde

The expected product is obtained in accordance with the procedure described in Preparation A, starting from 5-hydroxy-2-nitrobenzaldehyde and 1-(2-chloroethyl)-pyrrolidine.

Preparation D: 5-[N-(2-Dimethylaminoethyl)-N-methylamino]-2-nitrobenzaldehyde

The expected product is obtained in accordance with the procedure described in Preparation A, starting from 5-amino-2-nitrobenzaldehyde and 2-chloro-N,N-dimethyl-ethanamine hydrochloride.

Preparation E: 5-(2-Diethylaminoethoxy)-2-nitrobenzaldehyde

The expected product is obtained in accordance with the procedure described in Preparation A, starting from 5-hydroxy-2-nitrobenzaldehyde and 2-chloro-N,N-diethyl-ethanamine hydrochloride.

EXAMPLE 1

(10Z)-8-(2-Dimethylaminoethoxy)-2,3-dimethoxyindeno[1,2-b]indole-10(5H)-one O-(1-Phenyl-2-Propynyl)oxime Hydrochloride

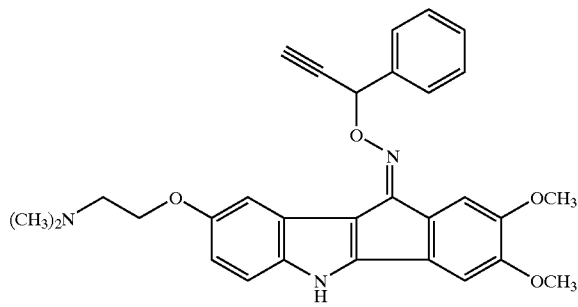

Step A: 3-Bromo-5,6-dimethoxyphthalide 12 mmol of N-bromosuccinimide are added to 10 mmol of 5,6-dimethoxyphthalide dissolved in dichloromethane, and then the reaction mixture, illuminated by a halogen lamp, is heated at reflux for 2 hours. The mixture is then brought to ambient temperature and filtered, and the filtrate is subsequently evaporated, toluene is added, and the suspension obtained is filtered and the filtrate evaporated to yield the expected product.

Step B: (5,6-Dimethoxyphthalidyl)triphenylphosphonium Bromide 10 mmol of triphenylphosphine are added to 10 mmol of the compound obtained in the above Step dissolved in toluene, and then the reaction mixture is heated at reflux for 3 hours. After returning to ambient temperature, the mixture is filtered and the cake obtained is then washed and dried to yield the expected product.

Melting point: >260° C.

Step C: 3-[5-(2-Dimethylaminoethoxy-2-nitrobenzylidene]-5, 6-dimethoxyphthalide 10 mmol of triethylamine and then, in portions, 10 mmol of the compound obtained in the above Step, are added to 10 mmol of the compound described in Preparation A dissolved in dimethylformamide. The reaction mixture is then heated at 50° C. for 1 hour 30 minutes, and subsequently brought to ambient temperature and evaporated. Ether is then added, and the mixture is stirred for one night and subsequently filtered. The cake obtained is then washed to yield the expected product.

Step D: 2-[5-(2-Dimethylaminoethoxy-2-nitrophenyl]-3-hydroxy-5,6-dimethoxy-1H-inden-1-one Hydrochloride 10 ml of a 4N sodium hydroxide solution are added to 10 mmol of the compound obtained in the above Step dissolved in methanol. The mixture is then brought to 40° C. for 1 hour, and subsequently cooled to 0° C. and adjusted to a pH of 1 using a 4N hydrochloric acid solution (12 ml). After stirring for 3 hours at 0° C., the white precipitate that has formed is filtered off and washed and then dried to yield the expected product.

Melting point: 23]° C.

Step E: 8-(2-Dimethylaminoethoxy)-2,3-dimethoxyindeno[1,2-b]indole-10(5H)-one Hydrochloride 10 mmol of triethylamine are added to 10 mmol of the compound obtained in the above Step suspended in dimethylformamide. The resulting solution is then placed under hydrogen in the presence of Raney nickel. After removal of the catalyst by filtration, 10 ml of a 1N hydrochloric acid solution are added, and then the solvents are evaporated off. The residue obtained is subsequently taken up in ethanol and then 1N hydrochloric acid is added. After filtration, the precipitate obtained is washed and dried to yield the expected product.

Melting point: >260° C.

Elemental microanalysis:

|  | C % | H % | N % | Cl % |
|---|---|---|---|---|
| calculated | 62.60 | 5.77 | 6.95 | 8.80 |
| found | 62.00 | 5.72 | 6.90 | 8.94 |

Step E: (10Z)-8-(2-Dimethylaminoethoxy)-2,3-dimethoxyindeno[1,2-b]indole-10(5H)-one O-(1-Phenyl-2-propynyl)oxime Hydrochloride 10 mmol of O-(1-phenyl-2-propynyl)hydroxylamine hydrochloride are added to 10 mmol of the compound obtained in the above Step dissolved in methanol. After having been stirred for 6 hours at ambient temperature, the reaction mixture is filtered. The cake is washed and then dried to yield the expected product.

Melting point: 226° C.

Elemental microanalysis:

|  | C % | H % | N % | Cl % |
|---|---|---|---|---|
| calculated | 67.73 | 5.68 | 7.90 | 6.66 |
| found | 67.82 | 5.74 | 7.97 | 6.76 |

EXAMPLE 2

(10Z)-8-(2-Dimethylaminoethoxy)-2,3-dimethoxyindeno[1,2-b]indole-10(5H)-one Oxime Hydrochloride The expected product is obtained in accordance with the procedure described in Step F of Example 1, starting from the compound described in Step E of Example 1 and hydroxylamine hydrochloride.

Melting point: >260° C.

Elemental microanalysis:

|  | C % | H % | N % | Cl % |
|---|---|---|---|---|
| calculated | 60.36 | 5.79 | 10.06 | 8.48 |
| found | 60.35 | 5.77 | 9.97 | 8.52 |

EXAMPLE 3

(10Z)-8-(2-Dimethylaninoethoxy)-2,3-dimethoxyindeno[1,2-b]indole-10(5-one O-Methyloxime Hydrochloride The expected product is obtained in accordance with the procedure described in Step F of Example 1, starting from the compound described in Step E of Example 1 and O-methyl-hydroxylamine hydrochloride Melting point: 250° C.

Elemental microanalysis:

|  | C % | H % | N % | Cl % |
|---|---|---|---|---|
| calculated | 61.18 | 6.07 | 9.73 | 8.21 |
| found | 60.80 | 6.06 | 9.59 | 8.31 |

EXAMPLE 4

(10Z)-8-(2-Dimethylaminoethoxy)-2,3-dimethoxyindeno[1,2-b]indole-10(5H)-one O-Allyloxime Hydrochloride The expected product is obtained in accordance with the procedure described in Step F of Example 1, starting from the compound described in Step E of Example 1 and O-allyl-hydroxylamine hydrochloride.

Melting point: >260° C.

Elemental microanalysis:

|  | C % | H % | N % | Cl % |
|---|---|---|---|---|
| calculated | 62.95 | 6.16 | 9.18 | 7.74 |
| found | 62.75 | 6.21 | 9.01 | 7.86 |

EXAMPLE 5

(10Z)-8-(2-Dimethylaminoethoxy)-2,3-dimethoxyindeno[1,2-b]indole-10(5H)-one O-Benzyloxime The expected product is obtained in accordance with the procedure described in Step F of Example 1, starting from the compound described in Step E of Example 1 and O-benzyl-hydroxylamine hydrochloride.

Melting point: 165° C.

Elemental microanalysis:

|  | C % | H % | N % |
|---|---|---|---|
| calculated | 71.32 | 6.20 | 8.91 |
| found | 71.62 | 6.42 | 8.84 |

EXAMPLE 6

(10Z)-8-(2-Dimethylaminoethoxy)-2,3-dimetoxyindeno[1,2-b]indole-10(5H)-one O-Phenyloxime The expected product is obtained in accordance with the procedure described in Step F of Example 1, starting from the compound described in Step E of Example 1 and O-phenyl-hydroxylamine hydrochloride.

Melting point: 174° C.

Elemental microanalysis:

|  | C % | H % | N % |
|---|---|---|---|
| calculated | 70.88 | 5.95 | 9.18 |
| found | 70.59 | 5.96 | 9.15 |

EXAMPLE 7

(10Z)-8-(2-Dimethylaminoethoxy)-2,3-dimethoxyindeno[1,2-b]indole-10(5H)-one O-(4-Nitrobenzyl)oxime The expected product is obtained in accordance with the procedure described in Step F of Example 1, starting from the compound described in Step E of Example 1 and O-(4-nitrobenzyl)hydroxylamine hydrochloride.

Melting point: 216° C.

Elemental microanalysis:

|  | C % | H % | N % |
|---|---|---|---|
| calculated | 65.11 | 5.46 | 10.85 |
| found | 64.96 | 5.47 | 10.83 |

EXAMPLE 8

(10Z)-(2-Dimethylamninoethoxy)-2,3-dimethoxyindeno[1,2-b]indole-10(5H)-one O-(3-Phenylallyl)oxime Hydrochloride The expected product is obtained in accordance with the procedure described in Step F of Example 1, starting from the compound described in Step E of Example 1 and O-(3-phenylallyl)hydroxylamine hydrochloride.
Melting point: 235° C.
Elemental microanalysis:

|  | C % | H % | N % | Cl % |
|---|---|---|---|---|
| calculated | 67.47 | 6.04 | 7.87 | 6.64 |
| found | 67.32 | 6.05 | 7.88 | 6.85 |

EXAMPLE 9

(10Z)-5-Allyl-8-(2-dimethylaminoethoxy)-2,3-dimetboxyindeno[1,2-b]indole-10(5H)-one O-Allyloxime Step A: 5-Allyl-8-(2-dimethylaminoethoxy)-2,3-dimethoxyindeno[1,2-b]indole-10(5H)-one 11 mmol of potassium carbonate are added to a solution of the compound described in Step E of Example 1 (10 mmol) in dimethylformamide, and then the reaction mixture is brought to 90° C. and 11 mmol of allyl bromide are added. The reaction mixture is then maintained at 60° C. for 1 night, and the solvent is subsequently evaporated off, water is added and the resulting suspension is filtered. The cake is then recrystallised to yield the expected product.
Melting point: 138° C.

Step B. (10Z)-5-Allyl-8-(2-dimethylaminoethoxy)-2,3-dimethoxyindeno[1,2-b]indole-10(5H)-one O-Allyloxime The expected product is obtained in accordance with the procedure described in Step F of Example 1, starting from the compound obtained in the above Step and O-allyl-hydroxylamine hydrochloride.
Melting point: 11° C.
Elemental microanalysis:

|  | C % | H % | N % |
|---|---|---|---|
| calculated | 70.26 | 6.77 | 9.10 |
| found | 70.09 | 6.72 | 9.11 |

EXAMPLE 10

(10Z)-8-(2-Dimethylaminoethoxy)-2,3-dimethoxyindeno[1,2-b]indole-10(5H)-one O-(3,4-Methylenedioxybenzyl)oxime The expected product is obtained in accordance with the procedure described in Step F of Example 1, starting from the compound described in Step E of Example 1 and O-(3,4-methylenedioxybenzyl)hydroxylamine hydrochloride.
Melting point: 108° C.
Elemental microanalysis:

|  | C % | H % | N % |
|---|---|---|---|
| calculated | 67.56 | 5.67 | 8.15 |
| found | 67.52 | 5.50 | 8.05 |

EXAMPLE 11

(10Z)-8-(2-Dimethylaminoethoxy)-2,3-dimethoxyindeno[1,2-b]indole-10(5H)-one O-(4-Methoxybenzyl)oxime The expected product is obtained in accordance with the procedure described in Step F of Example 1, starting from the compound described in Step E of Example 1 and O-(4-methoxybenzyl)hydroxylamine hydrochloride.
Melting point: 220° C.
Elemental microanalysis:

|  | C % | H % | N % |
|---|---|---|---|
| calculated | 69.44 | 6.23 | 8.38 |
| found | 69.15 | 6.26 | 8.33 |

EXAMPLE 12

(10Z)-8-(2-Dimethylaminoethoxy)-2,3-dimethoxyindeno[1,2-b]indole-10(5H)-one O-(3,5-Dimethylbenzyl)oxime The expected product is obtained in accordance with the procedure described in Step F of Example 1, starting from the compound described in Step E of Example 1 and O-(3,5-dimethylbenzyl)hydroxylamine hydrochloride.
Melting point: 181° C.
Elemental microanalysis:

|  | C % | H % | N % |
|---|---|---|---|
| calculated | 72.12 | 6.66 | 8.41 |
| found | 72.16 | 6.71 | 8.35 |

EXAMPLE 13

(10Z)-8-(2-Dimethylaminoethoxy)-2,3-dimethoxyindeno[1,2-b]indole-10(5H)-one O-(3,4,5-Trimethoxybenzyl)oxime The expected product is obtained in accordance with the procedure described in Step F of Example 1, starting from the compound described in Step E of Example 1 and O-(3,4,5-trimethoxybenzyl)hydroxylamine hydrochloride.
Melting point: 213° C.
Elemental microanalysis:

|  | C % | H % | N % |
|---|---|---|---|
| calculated | 66.30 | 6.28 | 7.48 |
| found | 66.62 | 6.32 | 7.39 |

EXAMPLE 14

(10Z)-8-(2-Dimethylaminoethoxy)-2,3-dimethoxyindeno[1,2-b]indole-10(5H)-one O-(1-Naphthylmethyl)oxime Hemihydrochloride The expected product is obtained in accordance with the procedure described in Step F of Example 1, starting from the compound described in Step E of Example 1 and O-(1-naphthylmethyl)hydroxylamine hydrochloride.

Melting point: 147° C.

Elemental microanalysis:

|  | C % | H % | N % | Cl % |
|---|---|---|---|---|
| calculated | 71.20 | 5.88 | 7.78 | 3.28 |
| found | 71.51 | 5.94 | 7.61 | 3.24 |

EXAMPLE 15

(10Z)-8-(2-Dimethylaminoethoxy)-2,3-dimethoxyindeno[1,2-b]indole-10(5H)-one O-(2-Thienylmethyl)oxime The expected product is obtained in accordance with the procedure described in Step F of Example 1, starting from the compound described in Step E of Example 1 and O-(2-thienylmethyl)hydroxylamine hydrochloride.

Melting point: 170° C.

Elemental microanalysis:

|  | C % | H % | N % | S % |
|---|---|---|---|---|
| calculated | 65.39 | 5.70 | 8.80 | 6.71 |
| found | 65.32 | 5.83 | 8.67 | 6.73 |

EXAMPLE 16

(10Z)-8-(2-Dimethylantinoethoxy)-2,3-dimethoxyindeno[1,2-b]indole-10(5H)-one O-Benzhydryloxime The expected product is obtained in accordance with the procedure described in Step F of Example 1, starting from the compound described in Step E of Example 1 and O-benzhydrylhydroxylamine hydrochloride.

Melting point: 234° C.

Elemental microanalysis:

|  | C % | H % | N % |
|---|---|---|---|
| calculated | 74.57 | 6.07 | 7.67 |
| found | 73.81 | 6.05 | 7.42 |

EXAMPLE 17

(10Z)-8-(2-Dimethylaminoethoxy)-2,3-dimethoxyindeno[1,2-b]indole-10(5H)-one O-(3-Phenyl-2-propynyl)oxime The expected product is obtained in accordance with the procedure described in Step F of Example 1, starting from the compound described in Step E of Example 1 and O-(3-phenyl-2-propynyl)hydroxylamine hydrochloride.

Melting point: 200° C.

Elemental microanalysis:

|  | C % | H % | N % |
|---|---|---|---|
| calculated | 72.71 | 5.90 | 8.48 |
| found | 72.79 | 5.94 | 8.47 |

EXAMPLE 18

(10Z)-8-(2-Dimethylaminoethoxy)-2,3-dimethoxyindeno[1,2-b]indole-10(5H)-one O-(2-Propynyl)oxime Hydrochloride The expected product is obtained in accordance with the procedure described in Step F of Example 1, starting from the compound described in Step E of Example 1 and O-(2-propynyl)hydroxylamine hydrochloride.

Melting point: 230° C.

Elemental microanalysis:

|  | C % | H % | N % | Cl % |
|---|---|---|---|---|
| calculated | 63.22 | 5.75 | 9.22 | 7.78 |
| found | 62.75 | 5.84 | 8.97 | 7.96 |

EXAMPLE 19

(10Z)-8-(2-Dimethylaminoethoxy)-2,3-dimetboxyindeno[1,2-b]indole-10(5H)-one O-(p-Tolyl)oxime Hydrochloride The expected product is obtained in accordance with the procedure described in Step F of Example 1, starting from the compound described in Step E of Example 1 and O-(p-tolyl)hydroxylamine hydrochloride.

Melting point: 190° C.

Elemental microanalysis:

|  | C % | H % | N % | Cl % |
|---|---|---|---|---|
| calculated | 66.20 | 5.95 | 8.27 | 6.98 |
| found | 66.64 | 5.89 | 8.20 | 7.07 |

EXAMPLE 20

(10Z)-8-(2-Dimethylaminoethoxy)-2,3-dimethoxyindeno[1,2-b]indole-10(5H)-one O-(3,5-Dimetboxyphenyl)oxime Hydrochloride The expected product is obtained in accordance with the procedure described in Step F of Example 1, starting from the compound described in Step E of Example 1 and O-(3,5-dimethoxyphenyl)hydroxylamine hydrochloride.

Melting point: 155° C.

Elemental microanalysis:

|  | C % | H % | N % | Cl % |
|---|---|---|---|---|
| calculated | 62.87 | 5.82 | 7.58 | 6.40 |
| found | 62.39 | 5.99 | 7.39 | 6.66 |

EXAMPLE 21

(10Z)-8-(2-Dimethylaminoethoxy)-2,3-dimethoxyindeno[1,2-b]indole-10(5H)-one O-[4-((E)-Styryl)benzyl]oxime Hydrochloride The expected product is obtained in accordance with the procedure described in Step F of Example 1, starting from the compound described in Step E of Example 1 and O-[4-((E)-styryl)benzyl]hydroxylamine hydrochloride.

Melting point: >260° C.

EXAMPLE 22

(10Z)-8-(2-Dimethylaminoethoxy)-2,3-dimethoxyindeno[1,2-b]indole-10(5H)-one O-(4-Phenoxybenzyl)oxime The expected product is obtained in accordance with the procedure described in Step F of Example 1, starting from the compound described in Step E of Example 1 and O-(4-phenoxybenzyl)hydroxylamine hydrochloride.

Melting point: 182° C.

Elemental microanalysis:

|  | C % | H % | N % |
|---|---|---|---|
| calculated | 72.45 | 5.90 | 7.45 |
| found | 72.41 | 5.84 | 7.45 |

EXAMPLE 23

(10Z)-8-(2-Dimethylaminoethoxy)-2,3-dimethoxyindeno[1,2-b]indole-10(5H)-one O-[(Biphenyl-4-yl)methyl]oxime Hydrochloride The expected product is obtained in accordance with the procedure described in Step F of Example 1, starting from the compound described in Step E of Example 1 and O-[(biphenyl-4-yl)methyl]hydroxylamine hydrochloride.

Melting point: >260° C.

Elemental microanalysis:

|  | C % | H % | N % | Cl % |
|---|---|---|---|---|
| calculated | 69.91 | 5.87 | 7.19 | 6.07 |
| found | 69.39 | 5.75 | 7.17 | 6.18 |

EXAMPLE 24

(10Z)-8-(2-Dimethylaminoethoxy)-2,3-dimetboxyindeno[1,2-b]indole-10(5H)-one O-(4-Benzyloxy-3-methoxybenzyl)oxime Hydrochloride The expected product is obtained in accordance with the procedure described in Step F of Example 1, starting from the compound described in Step E of Example 1 and O-(4-benzyloxy-3-methoxybenzyl)hydroxylamine hydrochloride.

Melting point: >260° C.

Elemental microanalysis:

|  | C % | H % | N % | Cl % |
|---|---|---|---|---|
| calculated | 67.13 | 5.95 | 6.52 | 5.50 |
| found | 66.91 | 5.89 | 6.54 | 5.60 |

EXAMPLE 25

(10Z)-8-(2-Dimethylaminoethoxy)-2,3-dimethoxyindeno[1,2-b]indole-10(5N)-one O-(2-Pyridylmethyl)oxime Hydrochloride The expected product is obtained in accordance with the procedure described in Step F of Example 1, starting from the compound described in Step E of Example 1 and O-(2-pyridylmethyl)hydroxylamine Melting point: 235° C.

Elemental microanalysis:

|  | C % | H % | N % | Cl % |
|---|---|---|---|---|
| calculated | 63.71 | 5.74 | 11.01 | 6.96 |
| found | 63.74 | 5.66 | 10.58 | 6.96 |

EXAMPLE 26

(10Z)-8-(2-Dimethylaminoethoxy)-2,3-dimethoxyindeno[1,2-b]indole-10(5H)-one N-Phenylhydrazone Hydrochloride The expected product is obtained in accordance with the procedure described in Step F of Example 1, starting from the compound described in Step E of Example 1 and N-phenyl-hydrazine hydrochloride.

Melting point: 200° C.

EXAMPLE 27

(10Z)-8-(2-Dimethylaminoethoxy)-2,3-dimethoxyindeno[1,2-b]indole-10(5H)-one O-[(2E)-5-Phenyl-2-penten-4-ynyl]oxime Hydrochloride The expected product is obtained in accordance with the procedure described in Step F of Example 1, starting from the compound described in Step E of Example 1 and O-[(2E)-5-phenyl-2-penten-4-ynyl]hydroxylamine hydrochloride.

Melting point: >250° C.

Elemental microanalysis:

|  | C % | H % | N % | Cl % |
|---|---|---|---|---|
| calculated | 68.87 | 5.78 | 7.53 | 6.35 |
| found | 68.88 | 5.81 | 7.53 | 6.46 |

EXAMPLE 28

(10Z)-8-(2-Dimethylaninoethoxy)-2,3-dimethoxyindeno[1,2-b]indole-10(5H)-one N-(4-Methoxyphenyl)hydrazone Hydrochloride The expected product is obtained in accordance with the procedure described in Step F of Example 1, starting from the compound described in Step E of Example 1 and N-(4-methoxyphenyl)hydrazine hydrochloride.

Melting point: 200° C.

Elemental microanalysis:

|  | C % | H % | N % | Cl % |
|---|---|---|---|---|
| calculated | 60.10 | 5.78 | 10.02 | 12.67 |
| found | 60.30 | 5.68 | 9.79 | 12.34 |

EXAMPLE 29

(10Z)-8-(2-Dimethylaminoethoxy)-2,3-dimethoxyindeno[1,2-b]indole-10(5H)-one O-(4-Fluorobenzyl)oxime Hydrochloride The expected product is obtained in accordance with the procedure described in Step F of Example 1, starting from the compound described in Step E of Example 1 and O-(4-fluorobenzyl)hydroxylamine hydrochloride.

Melting point: 162° C.

EXAMPLE 30

8-(2-Dimethylaminoethoxy)-2,3-dimethoxyindeno[1,2-b]indole-10(5H)-one O-[bis-(4-Fluorophenyl)methyl]oxime Sesquihydrochloride The expected product is obtained in accordance with the procedure described in Step F of Example 1, starting from the compound described in Step E of Example 1 and O-[bis-(4-fluorophenyl)methyl]hydroxylamine hydrochloride.

Elemental microanalysis:

|  | C % | H % | N % | Cl % |
|---|---|---|---|---|
| calculated | 64.05 | 5.10 | 6.59 | 8.16 |
| found | 63.38 | 4.80 | 6.62 | 8.33 |

EXAMPLE 31

8-(2-Dimethylaminoethoxy)-2,3-dimethoxyindeno[1,2-b]indole-10(5H)-one O-(1-Phenyl-3-butenyl)oxime Hydrochloride The expected product is obtained in accordance with the procedure described in Step F of Example 1, starting from the compound described in Step E of Example 1 and O-(1-phenyl-3-butenyl)hydroxylamine hydrochloride.

Elemental microanalysis:

|  | C % | H % | N % | Cl % |
|---|---|---|---|---|
| calculated | 67.94 | 6.25 | 7.67 | 6.47 |
| found | 68.06 | 6.13 | 7.60 | 6.68 |

EXAMPLE 32

(10Z)-8-(2-Dimethylaminoethoxy)-2,3-dimethoxyindeno[1,2-b]indole-10(5H)-one O-[3-(4-methoxyphenyl)-2-propynyl]oxime Hydrochloride The expected product is obtained in accordance with the procedure described in Step F of Example 1, starting from the compound described in Step E of Example 1 and O-[3-(4-methoxyphenyl)-2-propynyl]hydroxylamine hydrochloride.

Melting point: 236° C.

Elemental microanalysis:

|  | C % | H % | N % | Cl % |
|---|---|---|---|---|
| calculated | 66.24 | 5.74 | 7.48 | 6.31 |
| found | 65.72 | 5.69 | 7.42 | 5.63 |

EXAMPLE 33

(10Z)-8-(2-Dimethylaminoethoxy)-2,3-dimethoxyindeno[1,2-b]indole-10(5H)-one O-[1-(2-Phenylethynyl)-2-butynyl]oxime Hydrochloride The expected product is obtained in accordance with the procedure described in Step F of Example 1, starting from the compound described in Step E of Example 1 and O-[1-(2-phenylethynyl)-2-butynyl]hydroxylamine hydrochloride.

Melting point: 185° C.

Elemental microanalysis:

|  | C % | H % | N % | Cl % |
|---|---|---|---|---|
| calculated | 69.53 | 5.66 | 7.37 | 6.22 |
| found | 70.01 | 5.53 | 7.31 | 6.48 |

EXAMPLE 34

(10Z)-8-(2-Dimethylaminoethoxy)-2,3-dimethoxyindeno[1,2-b]indole-10(5H)-one O-[1-(4-Methoxyphenyl)-3-butenyl]oxime The expected product is obtained in accordance with the procedure described in Step F of Example 1, starting from the compound described in Step E of Example 1 and O-[1-(4-methoxyphenyl)-3-butenyl]hydroxylamine hydrochloride.

Melting point: 190° C.

EXAMPLE 35

(10Z)-8-(2-Dimethylaminoethoxy)-2,3-dimethoxyindeno[1,2-b]indole-10(5H)-one O-[3-(2-Thienyl)-2-propynyl]oxime Hydrochloride The expected product is obtained in accordance with the procedure described in Step F of Example 1, starting from the compound described in Step E of Example 1 and O-[3-(2-thienyl)-2-propynyl]hydroxylamine hydrochloride.

Melting point: >260° C.

EXAMPLE 36

(10Z)-8-(2-Dimethylaminoethoxy)-2,3-dimethoxyindeno[1,2-b]indole-10(5H)-one O-[1-((E)-Styryl)-3-butenyl]oxime The expected product is obtained in accordance with the procedure described in Step F of Example 1, starting from the compound described in Step E of Example 1 and O-[1-((E)-styryl)-3-butenyl]hydroxylamine hydrochloride.

Melting point: 176° C.

Elemental microanalysis:

|  | C % | H % | N % |
|---|---|---|---|
| calculated | 73.72 | 6.56 | 7.82 |
| found | 73.34 | 6.58 | 7.52 |

EXAMPLE 37

(10Z)-8-(2-Dimethylaminoethoxy)-2,3-dimethoxyindeno[1,2-b]indole-10(5H)-one O-(1-Phenyl-2-butynyl)oxime The expected product is obtained in accordance with the procedure described in Step F of Example 1, starting from the compound described in Step E of Example 1 and O-(1-phenyl-2-butynyl)hydroxyl amine hydrochloride.

Melting point: 216° C.

Elemental microanalysis:

|  | C % | H % | N % |
|---|---|---|---|
| calculated | 73.06 | 6.13 | 8.25 |
| found | 72.86 | 6.22 | 8.06 |

EXAMPLE 38

(10Z)-8-(2-Dimethylaminoethoxy)-2,3-dimethoxyindeno[1,2-b]indole-10(5H)-one O-[1-(p-Tolyl)-2-propynyl]oxime The expected product is obtained in accordance with the procedure described in Step F of Example 1, starting from the compound described in Step E of Example 1 and O-[1-(p-tolyl)-2-propynyl]hydroxylamine hydrochloride.

Melting point: 220° C.

Elemental microanalysis:

|  | C % | H % | N % |
|---|---|---|---|
| calculated | 73.06 | 6.13 | 8.25 |
| found | 72.80 | 6.12 | 8.17 |

EXAMPLE 39

(10Z)-8-(2-Dimethylaminoethoxy)-2,3-dimethoxyindeno[1,2-b]indole-10(5H)-one O[(1R)-1-Phenyl-2-propynyl]oxime Hydrochloride The expected product is obtained in accordance with the procedure described in Step F of Example 1, starting from the compound described in Step E of Example 1 and O-[(1R)-1-phenyl-2-propynyl]hydroxylamine hydrochloride.

EXAMPLE 40

(10Z)-8-(2-Dimethylaminoethoxy)-2,3-dimethoxyindeno[1,2-b]indole-10(5H)-one O[(1S)-1-Phenyl-2-propynyl]oxime Hydrochloride The expected product is obtained in accordance with the procedure described in Step F of Example 1, starting from the compound described in Step E of Example 1 and O-[(1S)-1-phenyl-2-propynyl]hydroxylamine hydrochloride.

EXAMPLE 41

8-(2-Dimethylaminoethoxy)-2,3-dimethoxyindeno[1,2-b]indole-10(5H)-one O-[1-(4-fluorophenyl)-2-propynyl]oxime Hydrochloride The expected product is obtained in accordance with the procedure described in Step F of Example 1, starting from the compound described in Step E of Example 1 and O-[1-(4-fluorophenyl)-2-propynyl]hydroxylamine hydrochloride.

Melting point: (Z/E mixture 86/14): 210° C.

Elemental microanalysis:

|  | C % | H % | N % | Cl % |
|---|---|---|---|---|
| calculated | 65.95 | 5.33 | 7.69 | 5.75 |
| found | 65.14 | 5.28 | 7.53 | 6.00 |

EXAMPLE 42

(10Z)-8-(2-Dimethylaminoethoxy)-2,3-dimethoxyindeno[1,2-b]indole-10(5H)-one O-(2-Butynyl)oxime Hydrochloride The expected product is obtained in accordance with the procedure described in Step F of Example 1, starting from the compound described in Step E of Example 1 and O-(2-butynyl)hydroxylamine hydrochloride.

Melting point: 230° C.

Elemental microanalysis:

|  | C % | H % | N % | Cl % |
|---|---|---|---|---|
| calculated | 63.89 | 6.01 | 8.94 | 6.73 |
| found | 63.98 | 5.98 | 8.91 | 6.54 |

EXAMPLE 43

(10Z)-8-(2-Dimethylaminoethoxy)-2,3-dimethoxyindeno[1,2-b]indole-10(5H)-one O-[1-(3-Thienyl)-2-propynyl]oxime Hydrochloride The expected product is obtained in accordance with the procedure described in Step F of Example 1, starting from the compound described in Step E of Example 1 and O-[1-(3-thienyl)-2-propynyl]hydroxylamine hydrochloride.

EXAMPLE 44

(10Z)-8-(2-Dimethylaminoethoxy)-2,3-dimethoxyindeno[1,2-b]indole-10(5H)-one O-(3-Butynyl)oxime The expected product is obtained in accordance with the procedure described in Step F of Example 1, starting from the compound described in Step E of Example 1 and O-(3-butynyl)hydroxylamine hydrochloride.

Melting point: 158° C.

Elemental microanalysis:

|  | C % | H % | N % |
|---|---|---|---|
| calculated | 69.27 | 6.28 | 9.69 |
| found | 68.81 | 6.15 | 9.19 |

EXAMPLE 45

(10Z)-8-(2-Dimethylaminoethoxy)-2,3-dimethoxyindeno[1,2-b]indole-10(5H)-one O-[1-(2-Thienyl)-2-propynyl]oxime Hydrochloride The expected product is obtained in accordance with the procedure described in Step F of Example 1, starting from the compound described in Step E of Example 1 and O-[1-(2-thienyl)-2-propynyl]hydroxylamine hydrochloride.

EXAMPLE 46

(10Z)-8-(2-Dimethylaminoethoxy)-2,3-dimethoxyindeno[1,2-b]indole-10(5H)-one O-(1-Methyl-2-propynyl)oxime Hydrochloride The expected product is obtained in accordance with the procedure described in Step F of Example 1, starting from the compound described in Step E of Example 1 and O-(1-methyl-2-propynyl)hydroxylamine hydrochloride.

Melting point: 253° C.

Elemental microanalysis:

|  | C % | H % | N % |
|---|---|---|---|
| calculated | 63.89 | 6.00 | 8.94 |
| found | 63.56 | 6.04 | 8.89 |

EXAMPLE 47

(10Z)-8-(2-Dimethylaminoethoxy)-2,3-dimethoxyindeno[1,2-b]indole-10(5H)-one O[1-(3-Pyridyl)-2-propynyl]oxime Dihydrochloride The expected product is obtained in accordance with the procedure described in Step F of Example 1, starting from the compound described in Step E of Example 1 and O-[1-(3-pyridyl)-2-propynyl]hydroxylamine hydrochloride.

Melting point: 164° C.

Elemental microanalysis:

|  | C % | H % | N % |
|---|---|---|---|
| calculated | 61.16 | 5.31 | 9.84 |
| found | 61.14 | 5.52 | 9.12 |

EXAMPLE 48

(10Z)-8-(2-Dimethylaminoethoxy)-2,3-dimethoxyindeno[1,2-b]indole-10(5H)-one O-Cyanomethyloxime Hydrochloride The expected product is obtained in accordance with the procedure described in Step F of Example 1, starting from the compound described in Step E of Example 1 and O-cyanomethylhydroxylamine hydrochloride.

Melting point: 242° C.

Elemental microanalysis:

|  | C % | H % | N % |
|---|---|---|---|
| calculated | 60.45 | 5.51 | 12.26 |
| found | 60.48 | 5.44 | 12.07 |

EXAMPLE 49

(10Z)-8-(2-Dimethylaminoethoxy)-2,3-dimethoxyindeno[1,2-b]indole-10(5H)-one O-(2,3,4,5,6-Pentafluorobenzyl)hydroxylamine The expected product is obtained in accordance with the procedure described in Step F of Example 1, starting from the compound described in Step E of Example 1 and O-(1-phenyl-2-butynyl)hydroxylamine hydrochloride.

Melting point: 177° C.

Elemental microanalysis:

|  | C % | H % | N % |
|---|---|---|---|
| calculated | 56.24 | 4.21 | 7.03 |
| found | 55.98 | 3.86 | 7.09 |

EXAMPLE 50

(10Z)-8-(2-Dimethylaminoethoxy)-2,3-dimethoxyindeno[1,2-b]indole-10(5H)-one O-[1-(4-Cyanophenyl)-2-propynyl]oxime Hydrochloride The expected product is obtained in accordance with the procedure described in Step F of Example 1, starting from the compound described in Step E of Example 1 and O-[1-(4-cyanophenyl)-2-propynyl]hydroxylamine hydrochloride.

Melting point: 183° C.

Elemental microanalysis:

|  | C % | H % | N % |
|---|---|---|---|
| calculated | 66.84 | 5.25 | 10.06 |
| found | 66.60 | 5.05 | 9.90 |

EXAMPLE 51

(10Z)-8-(2-Dimethylaminoethoxy)-2,3-dimethoxyindeno[1,2-b]indole-10(5H)-one O-[(4-Chloro-1,2,3-thiadiazol-5-yl)methyl]oxime Hydrochloride The expected product is obtained in accordance with the procedure described in Step F of Example 1, starting from the compound described in Step E of Example 1 and O-[(4-chloro-1,2,3-thiadiazol-5-yl)methyl]hydroxylamine hydrochloride.

Melting point: (Z/E mixture 90/10): 211° C.
Elemental microanalysis:

|  | C % | H % | N % | Cl % |
|---|---|---|---|---|
| calculated | 52.37 | 4.58 | 12.72 | 5.82 |
| found | 52.33 | 4.65 | 12.34 | 6.02 |

EXAMPLE 52

(10Z)-8-(2-Dimethylaminoethoxy)-2,3-dimethoxyindeno[1,2-b]indole-10(5H)-one O-[1-(3-Furyl)-2-propynyl]oxime Hydrochloride The expected product is obtained in accordance with the procedure described in Step F of Example 1, starting from the compound described in Step E of Example 1 and O-[1-(3-furyl)-2-propynyl]hydroxylamine hydrochloride.

Melting point: 225° C.

EXAMPLE 53

(10Z)-2,3-Dimethoxy-5-methyl-8-[2-(1-piperidyl)ethoxy]indeno[1,2-b]indole-10(5H)-one Oxime Hydrochloride Step A: 2,3-Dimethoxy-8-[2-(1-piperidyl)ethoxy]indeno[1,2-b]indole-10(5H)-one Hydrochloride The expected product is obtained in accordance with the procedure described in Steps C to E of Example 1, starting from the compound described in Step B of Example 1 and the compound described in Preparation B.

Melting point: >260° C.

Step B: 2,3-Dimethoxy-5-methyl-8-[2-(1-piperidyl)ethoxy]indeno[1,2-b]indole-10(5H)-one The expected product is obtained in accordance with the procedure described in Step A of Example 9, starting from the compound described in the above Step, with the replacement of allyl bromide with iodomethane.

Melting point: 200° C.

Step C: (10Z)-2,3-Dimethoxy-5-methyl-8-[2-(1-piperidyl)ethoxyindeno[1,2-b]indole-10(5H)-one Oxime Hydrochloride The expected product is obtained in accordance with the procedure described in Step F of Example 1, starting from the compound obtained in the above Step and hydroxylamine hydrochloride.

Melting point: 250° C.
Elemental microanalysis:

|  | C % | H % | N % |
|---|---|---|---|
| calculated | 63.76 | 6.21 | 8.92 |
| found | 63.65 | 6.36 | 8.73 |

EXAMPLE 54

(10Z)-2,3-Dimethoxy-8-[2-(1-pyrrolidinyl)ethoxy]indeno[1,2-b]indole-10(5H)-one O-Allyloxime Step A: 2,3-Dimethoxy-8-[2-(1-pyrrolidinyl)ethoxy]indeno[1,2-b]indole-10(5H)-one Hydrochloride The expected product is obtained in accordance with the procedure described in Steps C to E of Example 1, starting from the compound described in Step B of Example 1 and the compound described in Preparation C.

Melting point: 254° C.

Step B: (10Z)-2,3-Dimethoxy-8-[2-(1-pyrrolidinyl)ethoxy]indeno[1,2-b]indole-10(5H)-one O-Allyloxime The expected product is obtained in accordance with the procedure described in Step F of Example 1, starting from the compound obtained in the above Step and O-allylhydroxylamine hydrochloride.

Melting point: 169° C.
Elemental microanalysis:

|  | C % | H % | N % |
|---|---|---|---|
| calculated | 69.78 | 6.53 | 9.39 |
| found | 69.55 | 6.39 | 9.46 |

EXAMPLE 55

(10Z)-2,3-Dimethoxy-8-[2-(1-pyrrolidinyl)ethoxy]indeno[1,2-b]indole-10(5H)-one O-Tert-butyloxime The expected product is obtained in accordance with the procedure described in Step F of Example 1, starting from the compound obtained in Step A of Example 54 and O-tert-butylhydroxylamine hydrochloride.

Melting point: 197° C.
Elemental microanalysis:

|  | C % | H % | N % |
|---|---|---|---|
| calculated | 69.96 | 7.17 | 9.06 |
| found | 69.66 | 7.35 | 9.04 |

EXAMPLE 56

(10E)-8-(2-Dimethylaminoethoxy)-1,4-dimethoxyindeno[1,2-b]indole-10(5H)-one O-Benzyloxime Hydrochloride Step A: 8-(2-Dimethylaminoethoxy)-1,4-dimethoxyindeno[1,2-b]indole-10(5H)-one Hydrochloride The expected product is obtained in accordance with the procedure described in Steps A to E of Example 1, starting from 4,7-dimethoxyphthalide and the compound described in Preparation A.

Melting point: 230° C.

Step: (10E)-8-(2-Dimethylaminoethoxy)-1,4-dimethoxyindeno[1,2-b]indole-10(5H)-one O-Benzyloxime Hydrochloride The expected product is obtained in accordance with the procedure described in Step F of Example 1, starting from the compound obtained in the above Step and O-benzylhydroxylamine hydrochloride.

Melting point: 218° C.
Elemental microanalysis:

|  | C % | H % | N % | % Cl |
|---|---|---|---|---|
| calculated | 66.20 | 5.95 | 8.27 | 6.98 |
| found | 66.41 | 5.90 | 8.17 | 6.97 |

EXAMPLE 57

(10E)-8-(2-Dimethylaminoethoxy)-1,4-dimethoxyindeno[1,2-b]indole-10(5H)-one O-(1-Phenyl-2-propynyl)oxime Hydrochloride The expected product is obtained in accordance with the procedure described in Step F of Example 1, starting from the compound described in Step A of Example 56 and O-(1-phenyl-2-propynyl)hydroxylamine hydrochloride.
Melting point: 226° C.
Elemental microanalysis:

|  | C % | H % | N % | % Cl |
|---|---|---|---|---|
| calculated | 67.73 | 5.68 | 7.90 | 6.66 |
| found | 67.43 | 5.65 | 7.89 | 6.83 |

EXAMPLE 58

(10Z)-8-(2-Dimethylaminoethoxy)-2,3-methylenedioxyindeno[1,2-b]indole-10(5H)-one O-(2-Propynyl)oxime Hydrochloride The expected product is obtained in accordance with the procedure described in Example 1, starting from 5,6-methylenedioxyphthalide, the compound described in Preparation A and O-(2-propynyl)hydroxylamine hydrochloride.
Melting point: >260° C.
Elemental microanalysis:

|  | C % | H % | N % |
|---|---|---|---|
| calculated | 62.80 | 5.04 | 9.55 |
| found | 62.33 | 5.13 | 9.45 |

EXAMPLE 59

(10E)-8-(2-Dimethylaminoethoxy)-1,3-dimethoxyindeno[1,2-b]indole-10(5H)-one O-(2-Propynyl)oxime Hydrochloride The expected product is obtained in accordance with the procedure described in Example 1, starting from 4,6-dimethoxyphthalide, the compound described in Preparation A and O-(2-propynyl)hydroxylamine hydrochloride.
Melting point: 254° C.
Elemental microanalysis:

|  | C % | H % | N % |
|---|---|---|---|
| calculated | 63.22 | 5.75 | 9.22 |
| found | 63.42 | 6.17 | 9.16 |

EXAMPLE 60

(10E)-8-Hydroxy-1,3-dimethoxyindeno[1,2-b]indole-10(5H)-one O-(2-Propynyl)oxime hydrochloride
Step A: 8-Hydroxy-1,3-dimethoxyindeno[1,2-b]indole-10(5H)-one Hydrochloride
The expected product is obtained in accordance with the procedure described in Steps A to E of Example 1, starting from 4,6-dimethoxyphthalide and 5-hydroxy-2-nitrobenzaldehyde.
Melting point: 230° C.
Step B: (10E)-8-Hydroxy-1,3-dimethoxyindeno[1,2-b]indole-10(5H)-one O-(2-Propynyl)oxime HydrochlorideThe expected product is obtained in accordance with the procedure described in Step F of Example 1, starting from the compound obtained in the above Step and O-(2-propynyl)hydroxylamine hydrochloride.
Melting point: 174° C.
Elemental microanalysis:

|  | C % | H % | N % |
|---|---|---|---|
| calculated | 62.42 | 4.45 | 7.28 |
| found | 62.90 | 4.55 | 7.21 |

EXAMPLE 61

5-(2-Dimethylaminoethyl)-8-hydroxy-1,3-dimethoxyindeno[1,2-b]indole10(5H)-one O-(1-Phenyl-2-propynyl)oxime
Step A: 5-(2-Dimethylaminoethyl)-8-hydroxy-1,3-dimethoxyindeno[1,2-b]indole-10(5H)-one
The expected product is obtained in accordance with the procedure described in Step A of Example 9 starting from the compound described in Step A of Example 60, with the replacement of allyl bromide with 2-chloro-N,N-dimethylethanamine.
Step B: 5-(2-Dimethylaminoethyl)-8-hydroxy-1,3-dimethoxyindeno[1,2-b]indole-10(5H)-one O-(]-Phenyl-2-propynyl)oxime
The expected product is obtained in accordance with the procedure described in Step F of Example 1, starting from the compound obtained in the above Step and O-(1-phenyl-2-propynyl)hydroxylamine hydrochloride.
Melting point: (E/Z mixture 92/8): 128° C.
Elemental microanalysis:

|  | C % | H % | N % |
|---|---|---|---|
| calculated | 72.71 | 5.90 | 8.48 |
| found | 72.36 | 5.98 | 8.19 |

EXAMPLE 62

(10E)-5-(2-Dimethylaminoethyl)-8-hydroxy-1,3-dimethoxyindeno[1,2-b]indole-10(5H)-one O-Allyloxime The expected product is obtained in accordance with the procedure described in Step F of Example 1, starting from the compound described in Step A of Example 61 and O-allylhydroxylamine hydrochloride.
Melting point: 212° C.

EXAMPLE 63

(10Z)-2,3-Dimethoxy-8-hydroxyindeno[1,2-b]indole-10(5H)-one O-(2-Propynyl)oxime Hydrochloride
Step) A: 8-Hydroxy-2,3-dimethoxyindeno[1,2-b]indole-10(5H)-one Hydrochloride
The expected product is obtained in accordance with the procedure described in Steps C to E of Example 1, starting from the compound described in Step B of Example 1 and 5-hydroxy-2-nitrobenzaldehyde.
Step B: (10Z)-2,3-Dimethoxy-8-hydroxyindeno[1,2-b]indole-10(5H)-one O-(2-Propynyl)oxime Hydrochloride
The expected product is obtained in accordance with the procedure described in Step F of Example 1, starting from the compound obtained in the above Step and O-(2-propynyl)hydroxylamine hydrochloride.

Melting point: 156° C.

EXAMPLE 64

(10Z)-2,4-Dimethoxy-8-hydroxyindeno[1,2-b]indole-10(5H)-one O-(2-Propynyl)oxime

The expected product is obtained in accordance with the procedure described in Steps A to F of Example 1, starting from 5,7-dimethoxyphthalide, 5-hydroxy-2-nitrobenzaldehyde and O-(2-propynyl)hydroxylamine hydrochloride.

Melting point: 175° C.

Elemental microanalysis:

|  | C % | H % | N % |
|---|---|---|---|
| calculated | 68.96 | 4.63 | 8.04 |
| found | 68.81 | 4.62 | 7.84 |

EXAMPLE 65

(10E)-1,4-Dimethoxy-8-hydroxyindeno[1,2-b]indole-10(5H)-one O-(2-Propynyl)oxime

The expected product is obtained in accordance with the procedure described in Steps A to F of Example 1, starting from 4,7-dimethoxyphthalide, 5-hydroxy-2-nitrobenzaldehyde and O-(2-propynyl)hydroxylamine hydrochloride.

Elemental microanalysis:

|  | C % | H % | N % |
|---|---|---|---|
| calculated | 68.96 | 4.63 | 8.04 |
| found | 68.31 | 4.72 | 7.82 |

EXAMPLE 66

(10Z)-2,3-Dimethoxyindeno[1,2-b]indole-10(5H)-one O-(2-Dimethylaminoethyl)oxime Hydrochloride Step A: 2,3-Dimethoxyindeno[1,2-b]indole-10(5H)-one Hydrochloride The expected product is obtained in accordance with the procedure described in Steps C to E of Example 1, starting from the compound described in Step B of Example 1 and 2-nitrobenzaldehyde.

Step B: (10Z)-2,3-Dimethoxyindeno[1,2-b]indole-10(5H)-one O-(2-Dimethylaminoethyl)oxime Hydrochloride The expected product is obtained in accordance with the procedure described in Step F of Example 1, starting from the compound obtained in the above Step and O-(2-dimethylaminoethyl)hydroxylamine hydrochloride.

Melting point: 189° C.

Elemental microanalysis:

|  | C % | H % | N % | Cl % |
|---|---|---|---|---|
| calculated | 62.76 | 6.02 | 10.46 | 8.82 |
| found | 62.87 | 5.97 | 10.37 | 8.90 |

EXAMPLE 67

(10Z)-5-Allyl-2,3-dimethoxyindeno[1,2-b]indole10(5H)-one O-(2-Dimethylaminoethyl)oxime Step A: 5-Allyl-2,3-dimethoxyindeno[1,2-b]indole-10(5H)-one The expected product is obtained in accordance with the procedure described in Step A of Example 9, starting from the compound described in Step A of Example 66.

Step B: (10Z)-5-Allyl-2,3-dimethoxyindeno[1,2-b]indole-10(5H)-one O-(2-Dimethylaminoethyl)oxime The expected product is obtained in accordance with the procedure described in Step F of Example 1, starting from the compound obtained in the above Step and O-(2-dimethyl-aminoethyl)hydroxylamine hydrochloride.

Melting point: 111° C.;

Elemental microanalysis:

|  | C % | H % | N % |
|---|---|---|---|
| calculated | 71.09 | 6.71 | 10.36 |
| found | 71.18 | 6.86 | 10.17 |

EXAMPLE 68

(10Z)-2,3-Dimethoxy-8-hydroxy-5-methylindeno[1,2-b]indole-10(5H)-one O-(2-Propynyl)oxime The expected product is obtained in accordance with the procedure described in Steps B and C of Example 53, starting from the compound obtained in Step A of Example 63 and O-(2-propynyl)hydroxylamine hydrochloride.

Melting point: 134° C.

Elemental microanalysis:

|  | C % | H % | N % |
|---|---|---|---|
| calculated | 69.60 | 5.01 | 7.73 |
| found | 69.28 | 4.87 | 7.59 |

EXAMPLE 69

(10Z)-8-[N-(2-Dimethylaminoethyl)-N-methylamino]-2,3-dimethoxyindeno[1,2-b]indole-10(5H)-one O-(1-Phenyl-2-propynyl)oxime Dihydrochloride The expected product is obtained in accordance with the procedure described in Steps C to F of Example 1, starting from the compound obtained in Step B of Example 1, the compound described in Preparation D and O-(1-phenyl-2-propynyl)hydroxylamine hydrochloride.

EXAMPLE 70

(10Z)-2,3-Dimethoxy-8-hydroxy-5-methylindeno[1,2-b]indole-10(5H)-one O-(1-Phenyl-2-propynyl)oxime The expected product is obtained in accordance with the procedure described in Example 53, starting from the compound described in Step B of Example 1,5-hydroxy-2-nitrobenzaldehyde and O-(1-phenyl-2-propynyl)hydroxylamine hydrochloride.

Melting point: 23 7° C.

Elemental microanalysis:

|  | C % | H % | N % |
|---|---|---|---|
| calculated | 73.96 | 5.06 | 6.39 |
| found | 73.66 | 5.01 | 6.45 |

EXAMPLE 71

(10Z)-8-[N-(2-Dimethylaminoethyl)-N-methylamino]-2,3-dimethoxyindeno[1,2-b]indole-10(5H)-one O-(2-Propynyl)oxime Dihydrochloride The expected product is obtained in accordance with the procedure described in Steps C to F of Example 1, starting from the compound obtained in Step B of Example 1, the compound described in Preparation D and O-(2-propynyl)hydroxylamine hydrochloride.

Melting point: 155° C.

Elemental microanalysis:

|  | C % | H % | N % |
|---|---|---|---|
| calculated | 59.41 | 5.98 | 11.08 |
| found | 59.37 | 5.84 | 10.87 |

EXAMPLE 72

(10Z)-8-[N-(2-Dimethylaminoethyl)-N-methylamino]-2,3-dimethoxyindeno[1,2-b]indole-10(5H)-one O-(1-(2-Thienyl)-2-propynyl)oxime Dihydrochloride The expected product is obtained in accordance with the procedure described in Steps C to F of Example 1, starting from the compound obtained in Step B of Example 1, the compound described in Preparation D and O-(1-(2-thienyl)-2-propynyl)hydroxylamine hydrochloride.

Melting point: 201° C.

Elemental microanalysis:

|  | C % | H % | N % | S % |
|---|---|---|---|---|
| calculated | 59.28 | 5.49 | 9.54 | 5.46 |
| found | 59.33 | 5.45 | 9.68 | 5.05 |

EXAMPLE 73

(10Z)-5-Methyl-2,3,8-trimethoxyindeno[1,2-b]indole-10(5H)-one O-(3-Butynyl)oxime The expected product is obtained in accordance with the procedure described in Example 53, starting from the compound described in Step B of Example 1, 5-methoxy-2-nitrobenzaldehyde and O-(3-butynyl)hydroxylamine hydrochloride.

Elemental microanalysis:

|  | C % | H % | N % |
|---|---|---|---|
| calculated | 70.75 | 5.68 | 7.17 |
| found | 70.40 | 5.69 | 7.13 |

EXAMPLE 74

(10Z5-Methyl-2,3,8-trimethoxyindeno[1,2-b]indole-10(5H)-one O-(2-Propynyl)oxime

Step A: 2,3,8-Trimethoxyindeno[1,2-b]indole-10(5H)-one Hydrochloride

The expected product is obtained in accordance with the procedure described in Steps C to E of Example 1, starting from the compound described in Step B of Example 1 and 5-methoxy-2-nitrobenzaldehyde.

Step B: (10Z)-5-Methyl-2,3,8-trimethoxyindeno[1,2-b]indole-10(5H)-one O-(2-Propynyl)oxime The expected product is obtained in accordance with the procedure described in Steps B and C of Example 53, starting from the compound obtained in the above Step and O-(2-propynyl)hydroxylamine hydrochloride.

Melting point: 199° C.

Elemental microanalysis:

|  | C % | H % | N % |
|---|---|---|---|
| calculated | 70.20 | 5.36 | 7.44 |
| found | 70.38 | 5.39 | 7.37 |

EXAMPLE 75

(10Z)-2,3,8-Trimethoxyindeno[1,2-b]indole-10(5H)-one O-(1-Phenyl-2-propynyl)oxime The expected product is obtained in accordance with the procedure described in Step F of Example 1, starting from the compound obtained in Step A of Example 74 and O-(1-phenyl-2-propynyl)hydroxylamine hydrochloride.

Melting point: 203° C.

Elemental microanalysis:

|  | C % | H % | N % |
|---|---|---|---|
| calculated | 73.96 | 5.06 | 6.39 |
| found | 73.94 | 5.03 | 6.28 |

EXAMPLE 76

(10Z5-Methyl-2,3,8-trimethoxyindeno[1,2-b]indole-10(5H)-one O-(1-Phenyl-2-propynyl)oxime The expected product is obtained in accordance with Steps B and C of Example 53, starting from the compound obtained in Step A of Example 74 and O-(1-phenyl-2-propynyl)hydroxylamine hydrochloride.

Melting point: >250° C.

Elemental microanalysis:

|  | C % | H % | N % |
|---|---|---|---|
| calculated | 74.32 | 5.35 | 6.19 |
| found | 74.05 | 5.36 | 6.21 |

EXAMPLE 77

(10Z)-2,3,8-Trimethoxyindeno[1,2-b]indole-10(5H)-one O-(2-Propynyl)oxime

The expected product is obtained in accordance with the procedure described in Step F of Example 1, starting from the compound obtained in Step A of Example 74 and O-(2-propynyl)hydroxylamine hydrochloride.

Melting point: >250° C.

Elemental microanalysis:

|  | C % | H % | N % |
|---|---|---|---|
| calculated | 69.60 | 5.01 | 7.73 |
| found | 68.99 | 5.08 | 7.69 |

EXAMPLE 78

(10Z)-8-(2-Dimethylaminoethoxy)-2,3-diethoxyindeno[1,2-b]indole-10(5H)-one O-[1-(3-Furyl)-2-propynyl]oxime Hydrochloride Step A: (5,6-Diethoxyphthalidyl)triphenylphosphonium Bromide The expected product is obtained in accordance with the procedure described in Steps A and B of Example 1, starting from 5,6-diethoxyphthalide.

Step B: 8-(2-Dimethylaminoethoxy)-2,3-diethoxyindeno[1,2-b]indole-10(5H)-one Hydrochloride The expected product is obtained in accordance with the procedure described in Steps C to E of Example 1, starting from the compound obtained in the above Step and the compound described in Preparation A.

Step C: (10Z)-8-(2-Dimethylaminoethoxy)-2,3-diethoxyindeno[1,2-b]indole-10(5H)-one O-[1-(3-Furyl)-2-propynyl]oxime Hydrochloride The expected product is obtained in accordance with the procedure described in Step F of Example 1, starting from the compound obtained in the above Step and O-[1-(3-furyl)-2-propynyl]hydroxylamine hydrochloride.

Melting point: 225° C.

Elemental microanalysis:

|  | C % | H % | N % |
|---|---|---|---|
| calculated | 65.51 | 5.86 | 7.64 |
| found | 65.51 | 5.88 | 7.64 |

EXAMPLE 79

(10Z)-8-(2-Diethylaminoethoxy)-2,3-diethoxyindeno[1,2-b]indole-10(5H)-one O-[1-(3-Furyl)-2-propynyl]oxime Hydrochloride The expected product is obtained in accordance with the procedure described in Steps C to F of Example 1, starting from the compound obtained in Step A of Example 78, the compound described in Preparation E and O-[1-(3-furyl)-2-propynyl]hydroxylamine hydrochloride.

Melting point: 201° C.

Elemental microanalysis:

|  | C % | H % | N % |
|---|---|---|---|
| calculated | 66.48 | 6.28 | 7.27 |
| found | 66.16 | 6.28 | 7.26 |

EXAMPLE 80

(10Z)-2,3,8-Trimethoxyindeno[1,2-b]indole-10(5H)-one O-(2-Dimethylaminoethyl)oxime Dihydrochloride The expected product is obtained in accordance with the procedure described in Step F of Example 1, starting from the compound obtained in Step A of Example 74 and O-(2-dimethylaminoethyl)hydroxylamine hydrochloride.

Melting point: 242° C.

Elemental microanalysis:

|  | C % | H % | N % |
|---|---|---|---|
| calculated | 56.41 | 5.82 | 8.97 |
| found | 57.07 | 5.77 | 8.99 |

EXAMPLE 81

(10Z)-8-(2-Diethylaminoethoxy)-2,3-diethoxyindeno[1,2-b]indole-10(5H)-one O-[1-(3-Furyl)-2-propynyl]oxime Hydrochloride The expected product is obtained in accordance with the procedure described in Steps C to F of Example 1, starting from the compound obtained in Step B of Example 1, the compound described in Preparation E and O-[1-(3-furyl)-2-propynyl]hydroxylamine hydrochloride.

Melting point: 238° C.

Elemental microanalysis:

|  | C % | H % | N % |
|---|---|---|---|
| calculated | 65.51 | 5.86 | 7.64 |
| found | 65.22 | 5.97 | 7.77 |

EXAMPLE 82

(10Z)-8-[2-(1-Pyrrolidinyl)ethoxy]-2,3-dimetboxyindeno[1,2-b]indole-10(5H)-one O-[1-(3-Furyl)-2-propynyl]oxime Hydrochloride The expected product is obtained in accordance with the procedure described in Steps C to F of Example 1, starting from the compound obtained in Step B of Example 1, the compound described in Preparation C and O-[1-(3-furyl)-2-propynyl]hydroxylamine hydrochloride.

Melting point: 230° C.

Elemental microanalysis:

|  | C % | H % | N % |
|---|---|---|---|
| calculated | 65.75 | 5.52 | 7.67 |
| found | 65.95 | 5.47 | 7.92 |

EXAMPLE 83

(10Z)-8-[2-(1-Pyrrolidinyl)ethoxy]-2,3-dimetboxyindeno[1,2-b]indole-10(5H)-one O-[1-(3-Furyl)-2-propynyl]oxime Hydrochloride The expected product is obtained in accordance with the procedure described in Steps C to F of Example 1, starting from the compound obtained in Step A of Example 78, the compound described in Preparation C and O-[1-(3-furyl)-2-propynyl]hydroxylamine hydrochloride.

Melting point: 232° C.

Elemental microanalysis:

|  | C % | H % | N % |
|---|---|---|---|
| calculated | 66.72 | 5.95 | 7.29 |
| found | 66.29 | 6.06 | 7.21 |

EXAMPLE 84

(10Z)-8-(2-Dimethylaminoethoxy)-2,3-diethoxy-5-methyl-indeno[1,2-b]indole-10(5H)-one O-[1-(3-Furyl)-2-propynyl]oxime Hydrochloride The expected product is obtained in accordance with the procedure described in Steps B and C of Example 53, starting from the compound obtained in Step E of Example 1 and O-[1-(3-furyl)-2-propynyl]hydroxylamine hydrochloride.

Melting point: 242° C.

Elemental microanalysis:

|  | C % | H % | N % |
|---|---|---|---|
| calculated | 64.98 | 5.64 | 7.84 |
| found | 64.70 | 5.29 | 8.00 |

EXAMPLE 85

(10Z)-8-(2-Dimethylaminoethoxy)-2,3-diethoxyindeno[1,2-b]indole-10(5H)-one O-(1-Methyl-2-propynyl)oxime Hydrochloride The expected product is obtained in accordance with the procedure described in Step F of Example 1, starting from the compound described in Step B of Example 78 and O-(1-methyl-2-propynyl)hydroxylamine hydrochloride.

Melting point: 210° C.

Elemental microanalysis:

|  | C % | H % | N % |
|---|---|---|---|
| calculated | 65.12 | 6.48 | 8.44 |
| found | 64.79 | 6.49 | 8.50 |

EXAMPLE 86

(10Z)-8-(2-Dimethylaminoethoxy)-2,3-ethylenedioxyindeno[1,2-b]indole-10(5H)-one O-[1-(3-Furyl)-2-propynyl]oxime Hydrochloride Step A: 8-(2-Dimethylaminoethoxy)-2,3-ethylenedioxyindeno[1,2-b]indole-10(5H)-one Hydrochloride The expected product is obtained in accordance with the procedure described in Steps A to E of Example 1, starting from 5,6-ethylenedioxyphthalide and the compound described in Preparation A.

Step B: (10Z)-8-(2-Dimethylaminoethoxy)-2,3-ethylenedioxyindeno[1,2-b]indole-10(5H)-one O-[1-(3-Furyl)-2-propynyl]oxime hydrochloride The expected product is obtained in accordance with the procedure described in Step F of Example 1, starting from the compound obtained in the above Step and O-[1-(3-furyl)-2-propynyl]hydroxylamine hydrochloride.

EXAMPLE 87

(10Z)-8-(2-Dimethylaminoethoxy)indeno[1,2-b]indole-10(51)-one O-[1-(3Furyl)-2-propynyl]oxime Hydrochloride Step A: 8-(2-Dimethylaminoethoxy)indeno[1,2-b]indole-10(5H)-one Hydrochloride The expected product is obtained in accordance with the procedure described in Steps A to E of Example 1, starting from phthalide and the compound described in Preparation A.

Step B: (10Z)-8-(2-Dimethylaminoethoxy)indeno[1,2-b]indole-10(5H)-one O-[1-(3-Furyl)-2-propynyl]oxime Hydrochloride The expected product is obtained in accordance with the procedure described in Step F of Example 1, starting from the compound obtained in the above Step and O-[1-(3-furyl)-2-propynyl]hydroxylamine hydrochloride.

EXAMPLE 88

(10Z)-8-(2-Dimethylaminoethoxy)-2,3-ethylenedioxyindeno[1,2-b]indole-10(5H)-one O-[1-Methyl-2-propynyl]oxime Hydrochloride The expected product is obtained in accordance with the procedure described in Step F of Example 1, starting from the compound obtained in Step A of Example 86 and O-(1-Methyl-2-propynyl)hydroxylamine hydrochloride.

EXAMPLE 89

(10Z)-8-(2-Dimethylaminoethoxy)indeno[1,2-b]indole-10(51)-one O-[1-Methyl-2-propynyl]oxime Hydrochloride The expected product is obtained in accordance with the procedure described in Step F of Example 1, starting from the compound obtained in Step A of Example 87 and O-(1-methyl-2-propynyl)hydroxylamine hydrochloride.

EXAMPLE 90A (10Z)-8-(2-Dimethylaminoethoxy)-2,3-dimethoxyindeno[1,2-b]indole-10(5H)-one O-((1S)-1-Methyl-2-propynyl)oxime Hydrochloride The expected product is obtained in accordance with the procedure described in Step F of Example 1, starting from the compound described in Step E of Example 1 and O-[(1S)-1-methyl-2-propynyl]hydroxylamine hydrochloride.

Elemental microanalysis:

|  | C % | H % | N % |
|---|---|---|---|
| calculated | 63.89 | 6.00 | 8.94 |
| found | 63.48 | 5.88 | 8.72 |

EXAMPLE 90B (10Z)-8-(2-Dimethylaminoethoxy)-2,3-dimethoxyindeno[1,2-b]indole-10(5H)-one O-((1S)-1-Methyl-2-propynyl)oxime bis-Methanesulfonate The expected product is obtained by reaction of the hydrochloride compound of Example 90A with a base, followed by its salification by methanesulfonic acid.

Melting point: >260° C.

Elemental microanalysis:

|  | C % | H % | N % | S % |
|---|---|---|---|---|
| calculated | 51.83 | 5.64 | 6.72 | 10.25 |
| found | 51.79 | 5.69 | 6.68 | 10.41 |

EXAMPLE 90C (10Z)-8-(2-Dimethylaminoethoxy)-2,3-dimethoxyindeno[1,2-b]indole-10(5H)-one O-((1S)1-Methyl-2-propynyl)oxime Fumarate The expected product is obtained by reaction of the hydrochloride compound of Example 90A with a base, followed by its salification by fumaric acid.

EXAMPLE 90D (10Z)-8-(2-Dimethylaminoethoxy)-2,3-dimethoxyindeno[1,2-b]indole-10(5H)-one O-((1S)-1-Methyl-2-propynyl)oxime Tartrate The expected product is obtained by reaction of the hydrochloride compound of Example 90A with a base, followed by its salification by tartric acid.

EXAMPLE 91

(10Z)-8-(2-Dimethylaminoethoxy)-2,3-dimethoxyindeno[1,2-b]indole-10(5H)-one O-((1R)-1-Methyl-2-propynyl)oxime Hydrochloride The expected product is obtained in accordance with the procedure described in Step F of Example 1, starting from the compound described in Step E of Example 1 and O-[(1R)-1-methyl-2-propynyl]hydroxylamine hydrochloride.

Elemental microanalysis:

|  | C % | H % | N % |
|---|---|---|---|
| calculated | 63.89 | 6.00 | 8.94 |
| found | 63.77 | 5.95 | 8.74 |

EXAMPLE 92

(10Z)-8-(2-Dimethylaminoethoxy)-2,3-indeno[1,2-b]indole-10(5H)-one O-(1-Methyl-2-propynyl)oxime Hydrochloride The expected product is obtained in accordance with the procedure described in Step F of Example 1, starting from the compound described in Step A of Example 87 and O-(1-methyl-2-propynyl)hydroxylamine hydrochloride.

Melting point: 232–233° C.

Elemental microanalysis:

|  | C % | H % | N % |
|---|---|---|---|
| calculated | 67.39 | 5.90 | 10.25 |
| found | 67.15 | 5.62 | 10.39 |

EXAMPLE 93

(10Z)-8-(2-Dimethylaminoethoxy)-2,3-dimethoxyindeno[1,2-b]indole-10(5H)-one O-((1R)-1-Cyclopropyl-2-propynyl)oxime Hydrochloride The expected product is obtained in accordance with the procedure described in Step F of Example 1, starting from the compound described in Step E of Example 1 and O-(1-cyclopropyl-2-propynyl)hydroxylamine hydrochloride.

Melting point: 234° C.

Elemental microanalysis:

|  | C % | H % | N % |
|---|---|---|---|
| calculated | 65.38 | 6.10 | 8.47 |
| found | 64.57 | 5.99 | 8.30 |

EXAMPLE 94

(10Z)-8-(2-Dimethylaminoethoxy)-2,3-indeno[1,2-b]indole-10(5H)-one O-(1-Cyclopropyl-2-propynyl)oxime Hydrochloride The expected product is obtained in accordance with the procedure described in Step F of Example 1, starting from the compound described in Step A of Example 87 and O-(1-cyclopropyl-2-propynyl)hydroxylamine hydrochloride.

Melting point: 225° C.

Elemental microanalysis:

|  | C % | H % | N % |
|---|---|---|---|
| calculated | 68.88 | 6.01 | 9.64 |
| found | 68.46 | 5.89 | 9.51 |

EXAMPLE 95

(10Z)-8-(2-Dimethylaminoethoxy)-2,3-dimethoxyindeno[1,2-b]indole-10(5H)-one O-(1-Pentyl-2-propynyl)oxime Hydrochloride The expected product is obtained in accordance with the procedure described in Step F of Example 1, starting from the compound described in Step E of Example 1 and O-[1-pentyl-2-propynyl]hydroxylamine hydrochloride.

Melting point: 207° C.

Elemental microanalysis:

|  | C % | H % | N % |
|---|---|---|---|
| calculated | 66.21 | 6.90 | 7.99 |
| found | 66.51 | 6.86 | 8.00 |

EXAMPLE 96

(10Z)-8-(2-Dimethylaminoethoxy)-2,3-dimethoxyindeno[1,2-b]indole-10(5H)-one O-((1S)-1-Pentyl-2-propynyl)oxime Hydrochloride The expected product is obtained in accordance with the procedure described in Step F of Example 1, starting from the compound described in Step E of Example 1 and O-[(1S)-1-pentyl-2-propynyl]hydroxylamine hydrochloride.

Melting point: 202° C.

Elemental microanalysis:

|  | C % | H % | N % |
|---|---|---|---|
| calculated | 66.21 | 6.90 | 7.99 |
| found | 66.01 | 6.68 | 8.18 |

EXAMPLE 97

(10Z)-8-(2-Dimethylaminoethoxy)-2,3-dimethoxyindeno[1,2-b]indole-10(5H)-one O-((1R)-1-Pentyl-2-propynyl)oxime Hydrochloride The expected product is obtained in accordance with the procedure described in Step F of Example 1, starting from the compound described in Step E of Example 1 and O-((1R)-1-pentyl-2-propynyl)hydroxylamine hydrochloride.

Melting point: 202° C.

Elemental microanalysis:

|  | C % | H % | N % |
|---|---|---|---|
| calculated | 66.21 | 6.90 | 7.99 |
| found | 65.66 | 6.83 | 8.33 |

EXAMPLE 98

(10Z)-8-(2-Dimethylaminoethoxy)-2,3-dimethoxyindeno[1,2-b]indole-10(5H)-one O-(1-Ethyl-2-propynyl)oxime Hydrochloride The expected product is obtained in accordance with the procedure described in Step F of Example 1, starting from the compound described in Step E of Example 1 and O-[1-ethyl-2-propynyl]hydroxylamine hydrochloride.

Melting point: 244° C.

Elemental microanalysis:

|  | C % | H % | N % |
|---|---|---|---|
| calculated | 64.52 | 6.25 | 8.68 |
| found | 64.17 | 6.24 | 8.73 |

EXAMPLE 99

(10Z)-8-(2-Dimethylaminoethoxy)-2,3-dimethoxyindeno[1,2-b]indole-10(5H)-one O-(1-Isopropyl-2-propynyl)oxime Hydrochloride The expected product is obtained in accordance with the procedure described in Step F of Example 1, starting from the compound described in Step E of Example 1 and O-[1-isopropyl-2-propynyl]hydroxylamine hydrochloride.

Melting point: 235° C.

Elemental microanalysis:

|  | C % | H % | N % |
|---|---|---|---|
| calculated | 65.12 | 6.48 | 8.44 |
| found | 65.13 | 6.36 | 8.56 |

EXAMPLE 100

(10Z)-8-(2-Dimethylaminoethoxy)-2,3-dimethoxyindeno[1,2-b]indole-10(5H)-one O-(1-Isobutyl-2-propynyl)oxime Hydrochloride The expected product is obtained in accordance with the procedure described in Step F of Example 1, starting from the compound described in Step E of Example 1 and O-[1-isobutyl-2-propynyl]hydroxylamine hydrochloride.

Melting point: 202° C.

Elemental microanalysis:

|  | C % | H % | N % |
|---|---|---|---|
| calculated | 65.68 | 6.69 | 8.21 |
| found | 65.39 | 6.64 | 8.22 |

EXAMPLE 101

(10Z)-8-(2-Dimethylaminoethoxy)-2,3-dimethoxyindeno[1,2-b]indole-10(5H)-one O-(1-Ethynyl-2-propynyl)oxime Hydrochloride The expected product is obtained in accordance with the procedure described in Step F of Example 1, starting from the compound described in Step E of Example 1 and O-[1-ethynyl-2-propynyl]hydroxylamine hydrochloride.

EXAMPLE 102

(10Z)-8-(2-Dimethylaminoethoxy)-2,3-dimethoxyindeno[1,2-b]indole-10(5H)-one O-Trityl Oxime Hydrochloride Step A: O-Tritylhydroxylamine Hydrochloride The expected product is obtained in accordance with the procedure described in Tet.lett. 1997, 38, p. 7233, starting from trityl chloride.

Step B: (10Z)-8-(2-Dimethylaminoethoxy)-2,3-dimethoxyindeno[1,2-b]indole-10(5H)-one O-Trityl Oxime Hydrochloride The expected product is obtained in accordance with the procedure described in Step F of Example 1, starting from the compound described in Step E of Example 1 and the compound obtained in the above Step.

EXAMPLE 103

(10Z)-8-(2-Dimethylaminoethoxy)-2,3-dimethoxyindeno[1,2-b]indole-10(5H)-one O-(1,1-Dimethyl-2-propynyl)oxime Hydrochloride The expected product is obtained in accordance with the procedure described in Example 102, starting from the compound described in Step E of Example 1 and 3-chloro-3-methyl-1-butyne.

EXAMPLE 104

(10Z)-8-(2-Dimethylaminoethoxy)-2,3-dimethoxyindeno[1,2-b]indole-10(5H)-one O-(1-Ethyl-1-methyl-2-propynyl)oxime Hydrochloride The expected product is obtained in accordance with the procedure described in Example 102, starting from the compound described in Step E of Example 1 and 3-chloro-3-methyl-1-pentyne, the preparation of which is described in J. Org. Chem. 1955, 20, p. 95.

EXAMPLE 105

(10Z)-8-(2-Dimethylaminoethoxy)-2,3-dimethoxyindeno[1,2-b]indole-10(5H)-one O-(1-Ethynylcyclopentyl)oxime Hydrochloride The expected product is obtained in accordance with the procedure described in Example 102, starting from the compound described in Step E of Example 1 and 1-chloro-1-ethynylcyclopentane.

PHARMACOLOGICAL STUDY OF THE COMPOUNDS OF THE INVENTION

EXAMPLE 106

In vitro Cytotoxicity

Five cell lines were used:

2 murine leukaemias: L1210 and P388.

1 non-small-cell human lung carcinoma, A549.

1 human colon carcinoma, HT29.

1 human epidermoid carcinoma, A-431.

The cells are cultured in RPMI 1640 complete culture medium comprising 10% fetal calf serum, 2 mM glutamine, 50 units/ml of penicillin, 50 μg/ml of streptomycin and 10 mM Hepes, pH 7.4. The cells are distributed on microplates and are exposed to the cytotoxic compounds. The cells are then incubated for four doubling periods (2 days: L1210, P388, or 4 days: A549, HT29, A-431). The number of viable cells is then quantified by a colorimetric assay, the microculture tetrazolium assay (Cancer Res. 1987, 47 939–942).

The results are expressed as $IC_{50}$, the concentration of product that inhibits the proliferation of the treated cells by 50% compared with the untreated cells. By way of example, the compounds of Examples 1 and 18 have the $IC_{50}$ values mentioned in the Table below:

|  | $IC_{50}$ nM | | | | |
|---|---|---|---|---|---|
| Compounds tested | L1210 | P388 | A549 | HT29 | A-431 |
| Example 1 | 77 | 221 | 71 | 248 | 87 |
| Example 18 | 104 | 241 | 101 | 181 | 174 |

EXAMPLE 107

Action on the Cell Cycle (L1210)

L1210 cells are incubated for 21 hours at 37° C. in the presence of various concentrations of compound tested. The cells are then fixed using 70% ethanol (v/v), washed twice in PBS and incubated for 30 minutes at 20° C. in PBS that contains 100 μg/ml of RNAse and 50 μg/ml of propidium iodide. The distribution of the cells in the various phases of the cell cycle are then analysed by flow cytometry. The results are expressed as a percentage of the cells that have accumulated in the G2+M phase after 21 hours compared with the control (control: 20%). By way of example, at a concentration of 0.25 μM the compounds of Examples 1 and 18 induce a 75% accumulation of the cells in the G2+M phase after 21 hours.

EXAMPLE 108

In vivo Activity: Anti-tumour Activity of the Compounds on P388 Leukaemia

Line P388 (murine leukaemia) was supplied by the National Cancer Institute (Frederick, USA). The tumour cells ($10^6$ cells) were inoculated on day 0 by the i.p. route into the peritoneal cavity of female BDF1 mice (Iffa-Credo, France) weighing from 18 to 20 g (groups of 6 animals). The products were administered by the intravenous route on days 1, 5 and 9 at the doses indicated.

The anti-tumour activity is expressed as % T/C:

$$\% \ T/C = \frac{\text{median survival time of the treated animals}}{\text{median survival time of the control animals}} \times 100$$

By way of example, the compounds of Examples 1 and 18 are very active from a dose of 50 mg/kg; they double the survival time of the treated animals (T/C≧200%)

EXAMPLE 109

In vivo Activity: Anti-tumour Activity of the Compounds on Established C38 Colon Carcinoma Fragments of C38 colon carcinoma weighing approximately 30 mg were grafted subcutaneously on day 0 onto B6D2F1 mice (Iffa Credo, France). After growth of the tumour, the mice were separated into control (18 animals) and treated (6 to 7 animals) groups, which were homogeneous in respect of the tumour size. The products were administered by the i.v. route once a week for 3 weeks (on days 10, 17 and 24) at their maximum tolerated dose (MTD), MTD/2 and MTD/4.

The tumours were measured twice per week and the tumour volumes were calculated according to the formula: volume (mm$^3$)=length (mm)×width$^2$ (mm$^2$)/2.

The anti-tumour activity is expressed as % T/C:

$$\% \ T/C = \frac{\text{median } Vt/V0 \text{ of the treated animals}}{\text{median } Vt/V0 \text{ of the control animals}} \times 100$$

V0 and Vt denoting, respectively, the initial volume of the tumour and its volume at the time of measurement t.

The optimum dose is the dose that yields the lowest T/C without toxicity (premature death or loss of weight greater than 20%).

By way of example, the compound of Example 18 is very active from a dose of 25 mg/kg (T/C=24%).

EXAMPLE 110

Pharmaceutical Composition

| | |
|---|---|
| Formulation for the preparation of 1000 tablets containing a dose of 10 mg compound of Example 1 | 10 g |
| hydroxypropyl cellulose | 2 g |
| wheat starch | 10 g |
| lactose | 100 g |
| magnesium stearate | 3 g |
| talc | 3 g |

We claim:
1. A compound selected from those of formula (I):

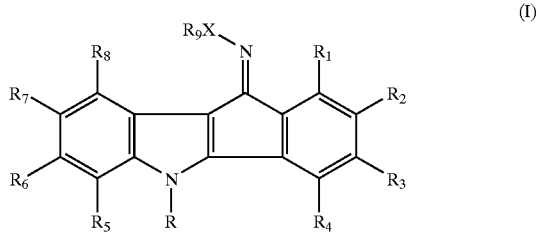

wherein:
R represents:
  hydrogen,
  linear or branched (C$_1$–C$_6$)alkyl optionally substituted by carboxy, by linear or branched (C$_1$–C$_6$) alkoxycarbonyl or by NR$_{10}$R$_{11}$ (wherein R$_{10}$ and R$_{11}$, which may be identical or different, each represents linear or branched (C$_1$–C$_6$)alkyl or together, with the nitrogen carrying them, form a nitrogen-containing heterocycle),
  or linear or branched (C$_1$–C$_6$)alkenyl,
R$_1$ to R$_8$, which may be identical or different, each represents:
  hydrogen,
  linear or branched (C$_1$–C$_6$)alkyl optionally substituted by aryl, carboxy or linear or branched (C$_1$–C$_6$) alkoxycarbonyl,
  hydroxy,
  linear or branched (C$_1$–C$_6$)acyloxy,
  a group of formula NR$_{12}$R$_{13}$, wherein R$_{12}$ and R$_{13}$, which may be identical or different, each represents hydrogen or linear or branched (C$_1$–C$_6$)alkyl optionally substituted by a group of formula NR$_{14}$R$_{15}$, wherein R$_{14}$ and R$_{15}$, which may be identical or different, each represents linear or branched (C$_1$–C$_6$) alkyl or together, with the nitrogen atom carrying them, form a nitrogen-containing heterocycle,
  carboxy,
  linear or branched (C$_1$–C$_6$)alkoxy optionally substituted by aryl or by a group of formula NR$_{14}$R$_{15}$, wherein R$_{14}$ and R$_{15}$, which may be identical or different, each represents linear or branched (C$_1$–C$_6$) alkyl or together, with the nitrogen atom carrying them, form a nitrogen-containing heterocycle,
  linear or branched (C$_1$–C$_6$)alkenyloxy,
  or one of R$_1$ to R$_8$ forms, with another of R$_1$ to R$_8$ that is adjacent, a (C$_1$–C$_2$)alkylenedioxy group,
X represents oxygen or NR$_{16}$, wherein R$_{16}$ represents hydrogen or linear or branched (C$_1$–C$_6$)alkyl, aryl or aryl-(C$_1$–C$_6$)alkyl in which the alkyl moiety may be linear or branched,
R$_9$ represents hydrogen, aryl, heteroaryl, or linear or branched (C$_1$–C$_6$)alkyl, wherein alkyl optionally contains one or more unsaturations and the alkyl is optionally substituted by one or more identical or different groups selected from aryl, heteroaryl, (C$_3$–C$_8$) cycloalkyl, cyano and NR$_{17}$R18 (wherein R$_{17}$ and R$_{18}$, which may be identical or different, each represents linear or branched (C$_1$—C$_6$)alkyl or together, with the nitrogen atom carrying them, form a nitrogen-containing heterocycle),
an isomer thereof, or an addition salt thereof with a pharmaceutically acceptable acid or base, wherein isomer is an optical isomer or geometrical isomer of the C=N X $R_9$, an aryl group is to be understood as:
  phenyl, biphenylyl or naphthyl, each of those groups optionally being substituted by one or more identical or different groups selected from halogen, linear or branched ($C_1$–$C_6$)alkyl (optionally substituted by one or more halogen), linear or branched ($C_1$–$C_6$)alkenyl (optionally substituted by phenyl), linear or branched ($C_1$–$C_6$)alkoxy (optionally substituted by phenyl), phenoxy, nitro, cyano, amino (optionally substituted by one or two linear or branched ($C_1$–$C_6$)alkyl) and ($C_1$–$C2$) alkylenedioxy, a heteroaryl group is to be understood as an aromatic mono- or bi-cyclic group having from 5 to 12 ring members containing one, two or three hetero atoms selected from oxygen, nitrogen and sulphur, wherein the heteroaryl may optionally be substituted by one or more identical or different groups selected from halogen, linear or branched ($C_1$–$C_6$)-alkyl, hydroxy, linear or branched ($C_1$–$C_6$)alkoxy, linear or branched ($C_1$–$C_6$) polyhaloalkyl, and amino (optionally substituted by one or more linear or branched ($C_1$–$C_6$)alkyl), and a nitrogen-containing heterocycle is to be understood as a saturated monocyclic group having from 5 to 7 ring members containing one, two or three hetero atoms, one of those hetero atoms being a nitrogen atom, and the additional hetero atom or atoms optionally present being selected from the atoms oxygen, nitrogen and sulphur.

2. A compound of claim 1, wherein X represents an oxygen atom.

3. A compound of claim 1, wherein $R_1$ to $R_6$ and $R_8$, which may be identical or different, each may be selected from hydrogen, hydroxy or linear or branched ($C_1$–$C_6$) alkoxy.

4. A compound of claim 1 wherein $R_7$ may be selected from 2-dimethylaminoethoxy or 2-(1-pyrrolidinyl)-ethoxy.

5. A compound of claim 1, which is (10Z)-8-(2-dimethylaminoethoxy)-2,3-dimethoxyindeno[1,2-b]indole-10(5H)-one O-(1-phenyl-2-propynyl)oxime, an isomer thereof, or an addition salt thereof with a pharmaceutically acceptable acid.

6. A compound of claim 1, which is (10Z)-8-(2-dimethylaminoethoxy)-2,3-dimethoxyindeno[1,2-b]indole-10(5H)-one O-(2-propynyl)oxime, an isomer thereof, or an addition salt thereof with a pharmaceutically acceptable acid.

7. A compound of claim 1, which is (10Z)-8-(2-dimethylaminoethoxy)-2,3-dimethoxyindeno[1,2-b]indole-10(5H)-one O-(1-methyl-2-propynyl)-oxime, an isomer thereof, or an addition salt thereof with a pharmaceutically acceptable acid.

8. A compound of claim 1, which is (10Z)-8-(2-dimethylaminoethoxy)-2,3-dimethoxyindeno[1,2-b]indole-10(5H)-one O-[1-(3-furyl)-2-propynyl]oxime, an isomer thereof, or an addition salt thereof with a pharmaceutically acceptable acid.

9. A compound of claim 1, which is (10Z)-8-[2-(1-pyrrolidinyl)ethoxy]-2,3-dimethoxyindeno[1,2-b]indole-10 (5H)-one O-[1-(3-furyl)-2-propynyl]oxime, an isomer thereof, or an addition salt thereof with a pharmaceutically acceptable acid.

10. A compound of claim 1, which is (10Z)-8-(2-dimethylamino-ethoxy)-2,3-dimethoxyindeno[1,2-b]indole-10(5H)-one O-((1S)-1-methyl-2-propynyl)oxime, an isomer thereof, or an addition salt thereof with a pharmaceutically acceptable acid.

11. A method for treating a living animal body afflicted with a cancer selected from leukemia, carcinoma, adenocarcinoma, and neuroblastoma, comprising the step of administering to the living animal body an amount of a compound of claim 1 which is effective for alleviation of the cancer.

12. A pharmaceutical composition, comprising as active principle, an effective amount of a compound of claim 1, together with one or more pharmaceutically acceptable excipients or vehicles.

* * * * *

UNITED STATES PATENT AND TRADEMARK OFFICE
CERTIFICATE OF CORRECTION

PATENT NO. : 6,627,650 B2
DATED : September 30, 2003
INVENTOR(S) : Michel Wierzbicki et al.

It is certified that error appears in the above-identified patent and that said Letters Patent is hereby corrected as shown below:

Title page,
Item [75], Inventors, "Nicolas Guilbaut" should be -- Nicolas Guilbaud --.

Column 42,
Line 61, "R18" should be -- $R_{18}$ --.

Column 43,
Line 13, "$(C_1-C2)$" should be -- $(C_1-C_2)$ --.

Signed and Sealed this

Eighteenth Day of November, 2003

JAMES E. ROGAN
*Director of the United States Patent and Trademark Office*